(12) United States Patent
Satoh et al.

(10) Patent No.: US 7,942,816 B2
(45) Date of Patent: May 17, 2011

(54) PSYCHOTIC MANIFESTATION AND MENTAL STATE EVALUATION APPARATUS AND EVALUATION METHOD

(75) Inventors: Shinji Satoh, Tsukuba (JP); Seiko Minoshita, Ushiku (JP); Toshiyuki Yamashita, Setagaya (JP)

(73) Assignees: Shinji Satoh, Ibaraki (JP); Seiko Minoshita, Ibaraki (JP)

( * ) Notice: Subject to any disclaimer, the term of this patent is extended or adjusted under 35 U.S.C. 154(b) by 697 days.

(21) Appl. No.: 11/500,978

(22) Filed: Aug. 9, 2006

(65) Prior Publication Data

US 2007/0050151 A1    Mar. 1, 2007

(30) Foreign Application Priority Data

Aug. 10, 2005   (JP) ................................ 2005-232622

(51) Int. Cl.
   *A61B 5/16*   (2006.01)
(52) U.S. Cl. ..................... 600/300; 434/236; 600/558
(58) Field of Classification Search ........................ None
   See application file for complete search history.

(56) References Cited

U.S. PATENT DOCUMENTS

| | | | |
|---|---|---|---|
| 2004/0220493 A1* | 11/2004 | Teicher et al. | 600/558 |
| 2005/0019734 A1* | 1/2005 | Peled | 434/236 |
| 2006/0178569 A1* | 8/2006 | Dean | 600/300 |

FOREIGN PATENT DOCUMENTS

JP   2004-298526   10/2004

OTHER PUBLICATIONS

"Brain Science", published by Seiwa Publishers 2000. (p. 177-181).
"Recognition of affect in facial expression using the Noh Mask Test: Comparison of individuals with schizophrenia and normal controls" by Seiko Minoshita, et al. Psychiatry and Clinical Neurosciences (2005), 59, 4-10.
"The Noh mask test for analysis of recognition of facial expression" by Seiko Minoshita, et al., Psychiatry and Clinical Neurosciences (1999), 53, 83-89.

* cited by examiner

*Primary Examiner* — Henry M Johnson, III
*Assistant Examiner* — Bobby Soriano
(74) *Attorney, Agent, or Firm* — Brundidge & Stanger, P.C.

(57) ABSTRACT

A psychotic manifestation and mental state evaluation apparatus and method which can individually discriminate among symptoms by taking advantage of stimulating Noh mask images and also evaluate with a high probability whether a person is suffering from a specific symptom at the time of diagnosing, clinical examination, assessment, or counseling.

23 Claims, 20 Drawing Sheets

PLOTTED DIAGRAM OF REACTION OF THE HEALTHY SUBJECT GROUP AND THE SCHIZOPHRENIC PATIENT GROUP TO NOH MASK EXPRESSIONS BY MULTIDIMENSIONAL SCALING
(DIMENSION 1, DIMENSION 2) U10: TILTING UP 10°, D30: TILTING DOWN 30°, FRONT: LOOKING STRAIGHT AHEAD.

EXAMINEE (K)
ANGLE OF STIMULATING IMAGE (J)
STATEMENT ITEM (I)

| HEALTHY SUBJECT | NOH MASK ANGLE→ | | | | | | | | |
| --- | --- | --- | --- | --- | --- | --- | --- | --- | --- |
| | TILTING DOWN | | | | | TILTING UP | | | |
| EMOTION ITEM | 40 | 30 | 20 | 10 | 0 | 10 | 20 | 30 | 40 |
| HATRED | + | | | | | | | | |
| SADNESS | | + | | | | | | | |
| SHY | | | + | | | | | | |
| CALMNESS | | | | + | | | | | |
| HAPPINESS | | | | | + | | | | |
| ABSENCE | | | | | | + | | | |
| SURPRISE | | | | | | + | | | |
| WEIRDNESS | | | | | | | + | | |
| FEAR | | | | | | | | + | |
| ANGER | | | | | | | | | + |

FIG. 7

| ORGANIC BRAIN DAMAGE | NOH MASK ANGLE→ | | | | | | | | |
|---|---|---|---|---|---|---|---|---|---|
| | TILTING DOWN | | | | | TILTING UP | | | |
| EMOTION ITEM | 40 | 30 | 20 | 10 | 0 | 10 | 20 | 30 | 40 |
| HATRED | | | | | | | | | |
| SADNESS | | | | | | | | | |
| SHY | | | | | | | | | |
| CALMNESS | | | | | | | | | |
| HAPPINESS | | | | | | | | − | − |
| ABSENCE | | | | | | | | | |
| SURPRISE | | | | | | | | | |
| WEIRDNESS | | | | | | | | | |
| FEAR | | | | | | | | | |
| ANGER | + | + | | | | | | | |

FIG. 8

| SCHIZOPHRENIA | NOH MASK ANGLE→ | | | | | | | | |
|---|---|---|---|---|---|---|---|---|---|
| | TILTING DOWN | | | | | TILTING UP | | | |
| EMOTION ITEM | 40 | 30 | 20 | 10 | 0 | 10 | 20 | 30 | 40 |
| HATRED | | | | | | + | | | − |
| SADNESS | | | | | | | | | |
| SHY | | | | | − | | | | |
| CALMNESS | | | | | | | | | |
| HAPPINESS | | | | | | | | | |
| ABSENCE | | | | | | | | | |
| SURPRISE | | | | | | | | | |
| WEIRDNESS | | | | | | | | | |
| FEAR | | | | | | | | | |
| ANGER | | | | | | | | | |

| DEPRESSIVE TENDENCY | NOH MASK ANGLE→ | | | | | | | | |
|---|---|---|---|---|---|---|---|---|---|
| | TILTING DOWN | | | | | TILTING UP | | | |
| EMOTION ITEM | 40 | 30 | 20 | 10 | 0 | 10 | 20 | 30 | 40 |
| HATRED | | | + | | | + | | | |
| SADNESS | | | | + | | | | | |
| SHY | | | | | | | | | |
| CALMNESS | | | | | | | | | |
| HAPPINESS | | | | | − | − | | | |
| ABSENCE | | | | | | | | | |
| SURPRISE | | | | | | | | | |
| WEIRDNESS | | | | | | | | | |
| FEAR | | | | | | | | | |
| ANGER | | | | | | | | | |

FIG. 10

NOH MASK ANGLE →

| EMOTION ITEM | TILTING DOWN | | | | 0 | TILTING UP | | | |
|---|---|---|---|---|---|---|---|---|---|
| | 40 | 30 | 20 | 10 | 0 | 10 | 20 | 30 | 40 |
| HATRED | HEALTHY+ | | DEP+ | | | SCHIZO+ DEP+ | | | SCHIZO- |
| SADNESS | | HEALTHY+ | | DEP+ | | | | | |
| SHY | | | HEALTHY+ | | SCHIZO- | | | | |
| CALMNESS | | | | HEALTHY+ | | | | | |
| HAPPINESS | | | | | HEALTHY+ DEP- | DEP- | | ORGANIC- | ORGANIC- |
| ABSENCE | | | | | | HEALTHY+ | | | |
| SURPRISE | | | | | | HEALTHY+ | | | |
| WEIRDNESS | | | | | | | HEALTHY+ | | |
| FEAR | | | | | | | | HEALTHY+ | |
| ANGER | ORGANIC+ | ORGANIC+ | | | | | | | HEALTHY+ |

HEALTHY:HEALTHY SUBJECTS, ORGANIC:PEOPLE WITH ORGANIC BRAIN DAMAGE,
SCHIZO:SCHIZOPHRENIC PEOPLE, DEP:PEOPLE WITH DEPRESSIVE TENDENCY

FIG. 17
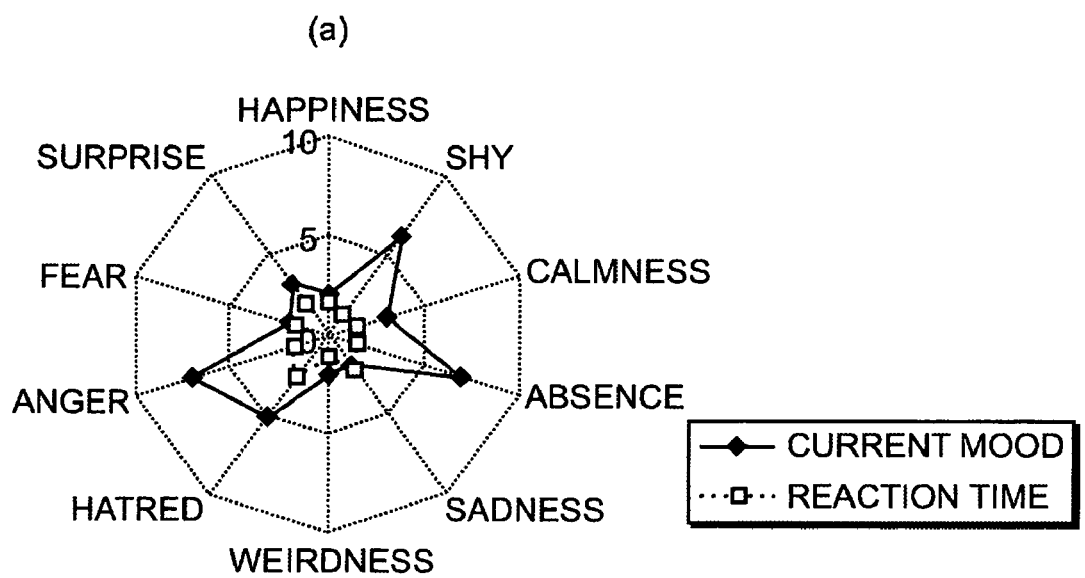
(a)
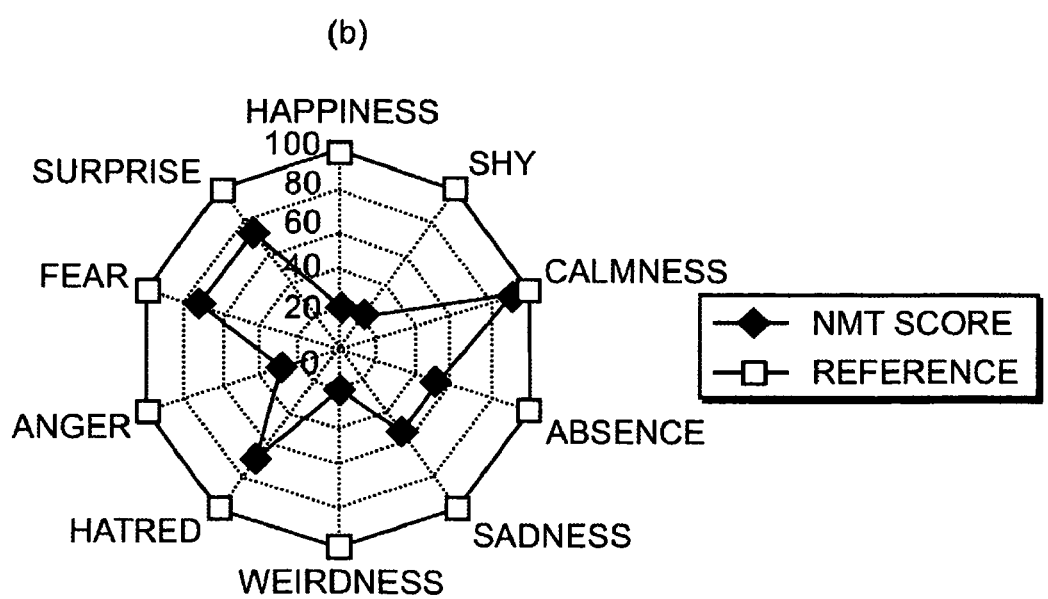
(b)

FIG. 20
(a)
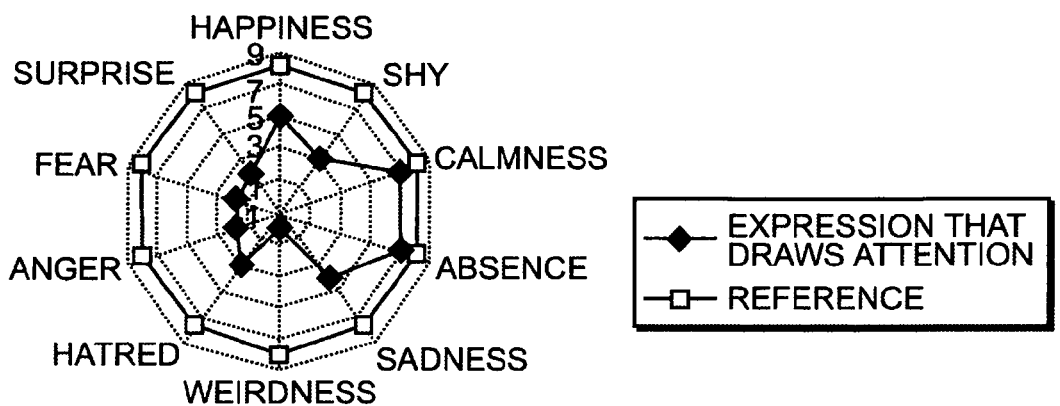
(b)
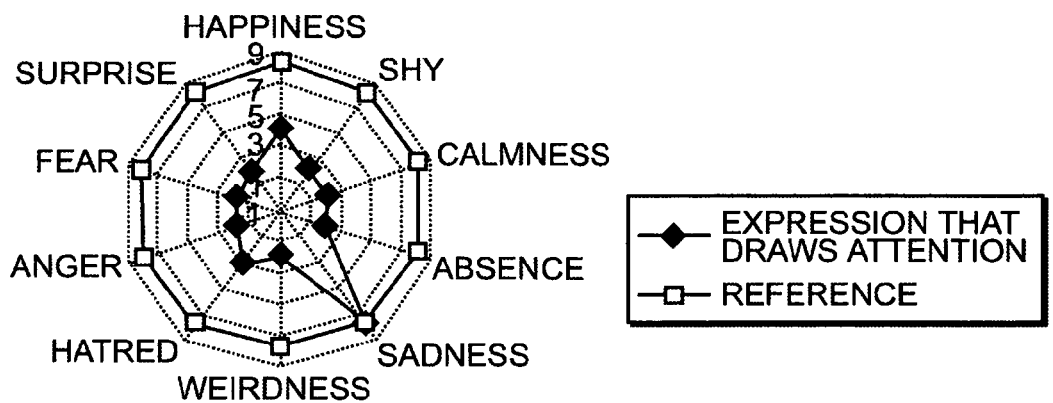
(c)
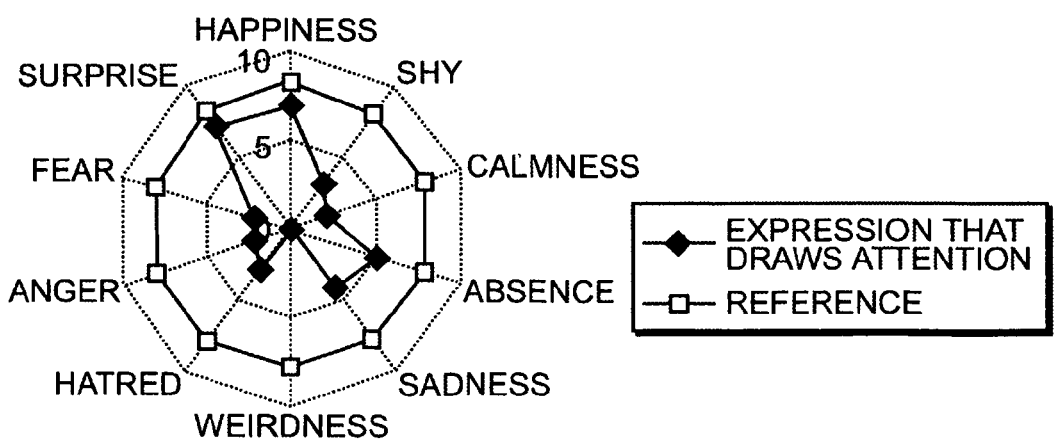

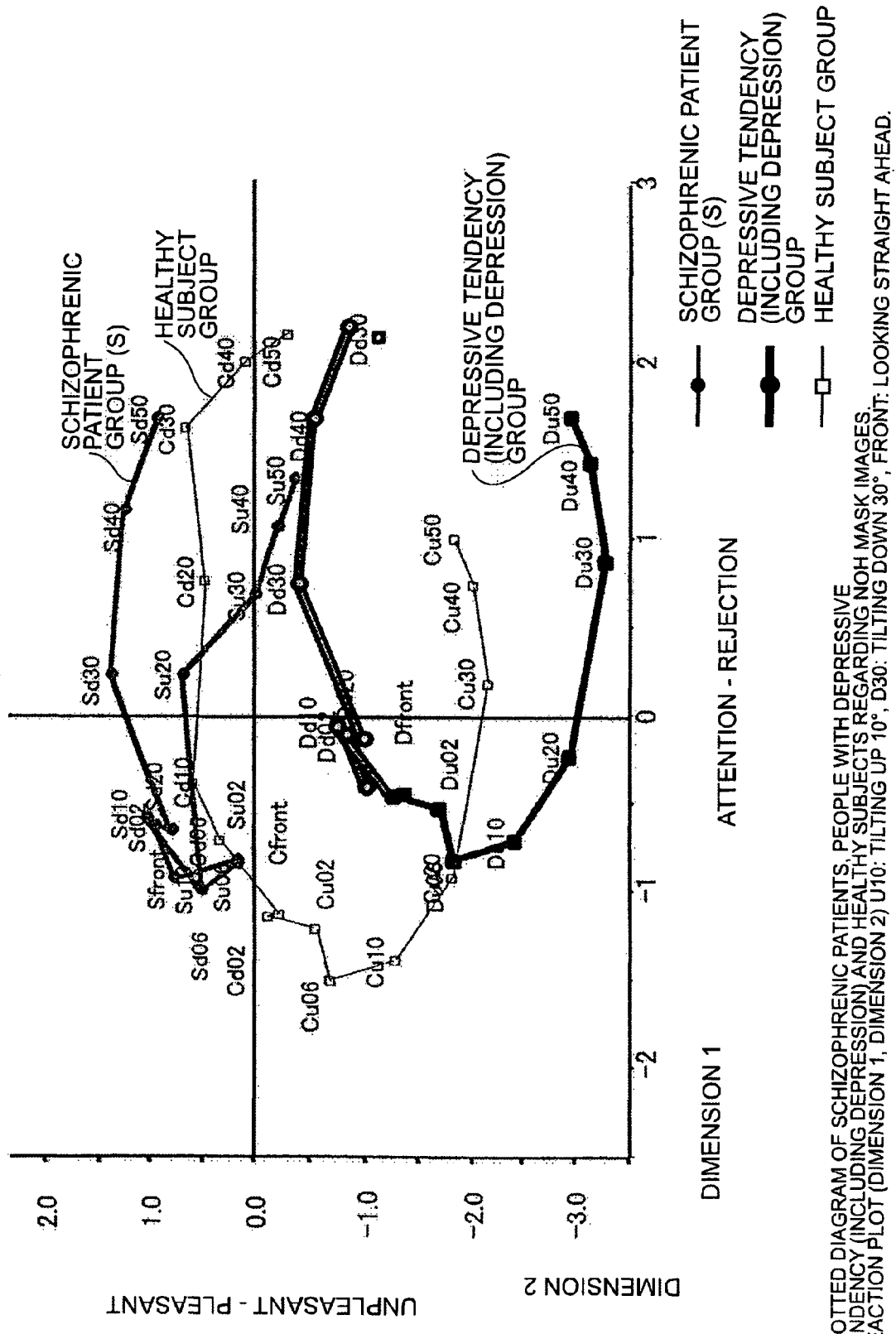

PLOTTED DIAGRAM OF REACTION OF THE HEALTHY SUBJECT GROUP AND THE SCHIZOPHRENIC PATIENT GROUP TO NOH MASK EXPRESSIONS BY MULTIDIMENSIONAL SCALING (DIMENSION 1, DIMENSION 2) U10: TILTING UP 10°, D30: TILTING DOWN 30°, FRONT: LOOKING STRAIGHT AHEAD.

PSYCHOTIC MANIFESTATION AND MENTAL STATE EVALUATION APPARATUS AND EVALUATION METHOD

FIELD OF THE INVENTION

The present invention relates to a psychotic manifestation and mental state evaluation apparatus and a psychotic manifestation and mental state evaluation method implemented by the evaluation apparatus.

BACKGROUND OF THE INVENTION

Research on expression cognition of schizophrenic patients has been actively carried out since the 1970s. Such research includes studies of various theories that say schizophrenic patients have an overall cognition disorder; their emotion cognition is generally deteriorating; only their negative emotion cognition is deteriorating; and their specific emotion is deteriorating. Additionally, there are studies that say the type of expression cognition differs depending on the clinical entity of schizophrenia as well as other studies that say schizophrenic patients do not have emotion cognition disorders. Therefore, there are ongoing arguments among the theories of schizophrenia that say patients cannot recognize all of the emotions expressed by other people, or that they cannot recognize specific emotions, or that their emotion cognition is not disordered at all.

The reference entitled "Related Articles, Links Perception of Facial Emotion in Schizophrenic and Right Brain-Damaged Patients", by Borod, et al., Journal of Nervous and Mental Disease, Aug. 1993, p. 181(8) and 494-502 discloses that the negative symptoms schizophrenic patients have are related to disorders of the right cerebral hemisphere. In addition, the hypothesis that schizophrenic patients have apathia and their expression cognition deteriorates has not been proven, and it has been suggested that there is no relationship between apathia and emotion cognition.

Thus, studies of an expression cognitive deficit in schizophrenic patients now include practical studies that focus on symptoms in addition to the argument about whether those patients have an overall emotion cognitive deficit. Currently, as the result of various discussions, there is a general consensus which concludes that schizophrenic patients have disorders in the ambiguous expression cognition.

The article entitled "The psychopathologic research of expression cognition", by S. Minoshita, et al. published in the February, 2000, issue of the "Brain Science" magazine by Seiwa Publishers, includes the following passages as part of the study of the expression cognition using Noh masks: "Herein, we will introduce our currently-developing research on the study of expression cognition using Noh masks. On the basis of Masuyama, Osaka and Suzuki's preceding study on images of Noh masks, we are currently conducting the following study.

In this experiment, we asked examinees to evaluate stimulating Noh mask images shown on a computer with respect to each of twelve statements (1. She is surprised, 2. She is sad, 3. She has hope, 4. She is shy, 5. She is putting a curse on me, 6. She is absent-minded, 7. She is enjoying herself, 8. She is interested in me, 9. She has pride, 10. She is depressed, 11. She is entranced, 12. She thinks I am weird) which the authors uniquely selected.

Fifteen Noh mask images photographed at different angles (down50, down40, down30, down20, down10, down6, down2, front, up2, up6, up10, up20, up30, up40, up48) were used within the range from tilting down 50 degrees to tilting up 48 degrees. In the experiment, a question was first given to an examinee, the point of regard was shown, and a Noh mask stimulating image was then shown and the image was displayed until the examinee answered "YES" or "NO".

Examinees include 15 healthy male subjects and 15 schizophrenic patients.

The obtained data was analyzed by using the multidimensional scaling (MDS) method. This is a commonly used method to arrange stimulating images for the study of emotions, and this method is also used in Schlosberg's emotion circular ring model. The resulting mapping shows two dimensions consisting of "pleasant-unpleasant" and "attention-rejection." (FIG. 1)"

In this application, the above-mentioned FIG. 1 is regarded as FIG. 23 which is the last drawing in this document.

Additionally, the above-mentioned description has been partially changed.

Next, in Japanese Application Laid-open Publication No. 2004-298526 which includes portions of the above-mentioned paper, there is a passage: "the mapping suggests that, for example, healthy subjects evaluate a Noh mask photographed at a downward angle of 50 degrees to be generally pleasant and rejective, whereas schizophrenic patients evaluate the same image generally unpleasant and rejective. As is the case with Schlosberg's emotion circular ring structure, the evaluation of the Noh mask images by healthy subjects creates an almost circular ring on the two dimensions consisting of "pleasant-unpleasant" and "attention-rejection". On the other hand, the evaluation by schizophrenic patients creates a semicircular which lacks a direction indicating "unpleasant". That is, schizophrenic patients do not consider a Noh mask having a malicious intent, but they tend to consider the mask as expressing rather favorable emotions. Therefore, schizophrenic patients tend to be slow in recognizing somebody's malicious intent, and there is the possibility that they may be cheated easily."

Japanese Application Laid-open Publication No. 2004-298526 discloses a schizophrenia diagnosis apparatus including a stimulation display means for providing an examinee with visual stimulation, a viewpoint identification means for identifying a viewpoint of the examinee with respect to the stimulation display means, a reactive search score calculation means for calculating reactive search scores from the results measured by the stimulation display means and the viewpoint identification means, a motion measuring means for measuring the number of motions from the results measured by the stimulation display means and the viewpoint identification means, and a means for diagnosing whether the examinee is suffering from schizophrenia or not based on the reactive search scores obtained by the reactive search score calculation means and the number of motions obtained by the number of motions measuring means.

In the psychiatric clinical examination or mental competency evaluation, the diagnosing, clinical examination, assessment, and counseling are carried out for people with organic brain damage, schizophrenics, depressives, people with personality disorder, dipsomaniacs, drug addicts, people with PTSD, and healthy subjects with depressive tendency who may able to be cured by counseling.

As stated above, the inventors of this application found out that the use of stimulating Noh mask images makes it possible to effectively judge whether a person is suffering from a mental disease or not. Furthermore, the inventors of this application have been engaged in the above-mentioned diagnosis, clinical examination, assessment, and counseling for a long time, and they have become keenly aware of the need to collectively judge the presence of symptoms at the time of the diagnosis, clinical examination, assessment, and counseling with regard to the above-mentioned symptoms in addition to individual evaluation of organic brain damage or schizophrenia. Specifically, it is important to quickly and accurately evaluate a large number of patients to determine whether they are suffering from organic brain damage, schizophrenia, or have depressive tendency (including depression) as well as evaluating the degree of depression. At present no such apparatus and method exists.

SUMMARY OF THE INVENTION

In the light of the above, the objective of the present invention is to provide a psychotic manifestation and mental state evaluation apparatus and an evaluation method which can individually evaluate various disorders by taking advantage of stimulating Noh mask images and also collectively evaluate with a high probability whether a person is suffering from a specific disorder at the time of diagnosing, clinical examination, assessment, or counseling.

The present invention provides a psychotic manifestation and mental state evaluation apparatus including a database which stores data of stimulating Noh mask images that express various kinds of human emotions according to changes of the angles at which the masks are photographed from the tilting up to tilting down, an image display apparatus for displaying the stimulating images, means for displaying questions (referred to as emotion items) about the feeling elicited by the stimulating images that have been one by one shown on the image display apparatus as well as displaying the response to each question, means for gathering statistical data of the response to each emotion item with respect to the emotion elicited by each stimulating image, and processing means for evaluating psychotic manifestation and mental state based on the gathered statistical data.

According to the present invention the database stores predetermined combinations of stimulating images photographed at different angles that have been selected from said stimulating images and plural emotion items that have been selected from said emotion items with respect to more than one psychotic manifestation and mental state. The processing means collects the reaction value and the reaction-time value from the response to each emotion item that corresponds to each stimulating image, and also collects the reaction data or/and reaction-time data by comparing those values with reference values, and then collects attention data from the reaction data or/and the reaction-time data with respect to each stimulating image, thereby creating attention data in regard to a specific emotion item with respect to a specific stimulating image. After the above, the processing means identifies a specific symptom based on the combination of the selected stimulating images and the emotion items comparing them with the stimulating image and emotion item stored in the database, and finally individual data is created for each specific symptom by including the comparison reaction data or/and reaction-time data of healthy subjects for a specific emotion item with respect to a specific symptom.

The present invention also provides an evaluation method that is implemented by the above described psychotic manifestation and mental state evaluation apparatus.

BRIEF DESCRIPTION OF THE DRAWINGS

The foregoing and a better understanding of the present invention will become apparent from the following detailed description of example embodiments and the claims when read in connection with the accompanying drawings, all forming a part of the disclosure of this invention. While the foregoing and following written and illustrated disclosure focuses on disclosing example embodiments of the invention, it should be clearly understood that the same is by way of illustration and example only and the invention is not limited thereto, wherein in the following brief description of the drawings:

FIG. 7 shows attention data with respect to organic brain damage;

FIG. 8 shows attention data with respect to schizophrenia;

FIG. 10 collectively shows attention data shown in FIG. 5 through FIG. 8;

FIG. 17 shows the expression circular ring structure model with respect to organic brain damage;

FIG. 20 shows the vocational profile (application to suitable vocation diagnosis system);

FIG. 22 shows an example of a two-dimensional drawing with respect to two symptoms.

DETAILED DESCRIPTION OF THE INVENTION

Figure 1:
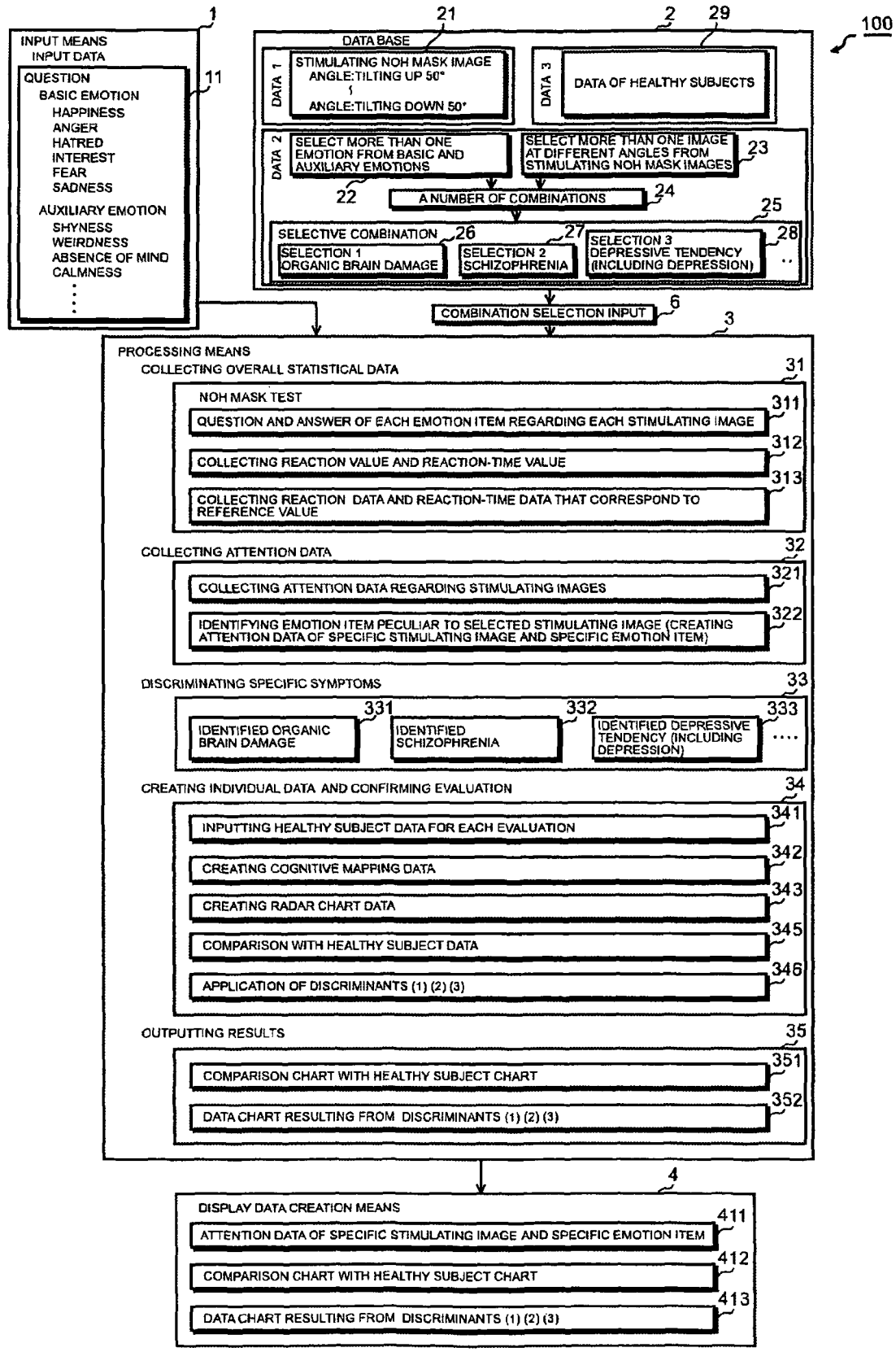
FIG. 1 is a block diagram that illustrates an embodiment of the present invention.

Noh masks are used in the Japanese traditional performing art, called Noh, and only a principal dancer called "Shite" wears a Noh mask on the Noh stage.

It is said that a Noh mask is a symbolic mask into which various elements of human being's face have been compounded and integrated and shows affluent emotional expressions that correspond to human emotions. A mask can change an expression as the viewing angle changes. In addition to Noh masks, there are other well-recognized masks in the world such as masks from Bali Island. Among Noh masks, only masks of female characters are made such that they show various expressions according to changes of the viewing angle (upward tilting mask is called "Terasu", and downward tilting mask is called "Kumorasu"). Among those female masks, a teenage-female face called "Koomote" that was used in the experiment is said to have the most variety of expressions. However, the mechanism of the expression cognition of both Noh masks and human faces has not been well defined, therefore it may be difficult to simply regard those two recognition mechanisms to be identical.

Furthermore, a Noh mask is made to express conflicting emotions, for example, when a mask tilts up, its mouth appears to turn down showing unpleasantness but its eyebrows and eyes appear to drop showing pleasantness; whereas when a Noh mask tilts down, its mouth appears to express pleasantness but its eyebrows and eyes appear to slant showing unpleasantness. Therefore, an examinee may have to make advanced judgment by comparing the expression on a Noh mask with a human being's face or line drawings of a human face and integrating the conflicting expressions of the Noh mask. However, almost identical factors were extracted from the results of the expression cognition factor analysis, which used healthy subjects as examinees and a Noh mask as a stimulation, which had been obtained from the inventors' preceding study (Minoshita et al., 1996) and from the results of the expression cognition factor analysis which used photos of human being's face as a stimulation in the preceding study.

For ten years, the inventors of this application have been engaged in making an effective tool for measuring the characteristics of the expression cognition of mentally disordered people, and the inventors finally succeeded in creating an expression cognition test that uses a Noh mask. The achievement appeared in "Human Engineering" (Vol. 33, No. 2, 79-86, 1997) and "Psychiatry and Clinical Neurosciences" (Vol. 53, No. 1, February, 1999). The outline is given below:

The inventors of this application were fortunate to borrow a Noh mask "Koomote" made in the Taisho era which was owned by Tomio TADA, honorary professor of Tokyo University. The Koomote was photographed by a professional photographer in a fully-equipped professional photo studio in Tsukuba University where the lighting apparatus was fully made available. Under the effective lighting conditions which actively changes expression of the Koomote, the Noh mask "Koomote" was affixed to a rotating device and photographed by measuring the angles of tilt by one degree at a time. For how to create the Noh mask test, refer to the separate document ("Human Engineering" Vol. 33, No. 2, 79-86, 1997). Then, reaction characteristics of healthy subjects were analyzed by using the factor analysis. The characteristics of the Noh mask test were investigated, and the emotion items used for the test were determined, thereby refining the Noh mask test method ("Psychiatry and Clinical Neurosciences" <Vol. 53, No. 1, February, 1999>).

After that, the inventors conducted a comparison with the YG personality test, a comparison with the angry behavior scales, and researched the relationship between self emotion and expression cognition (Minoshita S, Morita N, Satoh S, Asai Y. Relationships between facial expression recognition and social adjustment in schizophrenia.—The Noh mask test as a social skill assessment—Japanese Bulletin of Social Psychiatry 12(3)253-261, 2004), Japanese Academy of Facial Studies (Minoshita S, Yamashita T, Morita N, Sato S, Identifying expression of Noh mask associated with changes of angle of tilt, 1st Japanese Academy of Facial Studies, 1996.8.31, National Museum Shinjuku pavilion), impression engineering workshop (Minoshita S, Yamashita T, Morita N, Sato S, impression engineering research for expression cognition—impression engineering research of face by using a Noh mask—the relationship between facial image and mental state—, "Impression engineering" workshop, 1996.11.1, Fujitsu Cross-Cultural Center, Sensibility Technology Promotion Department of Fujitsu). Moreover, the inventors analyzed ambiguity of Noh mask expressions by using the fuzzy inference method, thereby exploring the possibility of making tools for cross-cultural communications (Yamashita T, Yoshikawa M, Minoshita S, Ichimura T, Satoh S, Automatic scenario analysis system for Noh play with Noh masks. KES '01 Baba N et al (Eds.) IOS Press, 983-987, 2001).

According to an embodiment of the present invention, it is possible to provide a psychotic manifestation and mental state evaluation method that uses a psychotic manifestation and mental state evaluation apparatus including:

a database which stores data of stimulating Noh mask images that express various kinds of human emotions according to changes of the angles at which the masks are photographed from the tilting up to tilting down, an image display apparatus for displaying the stimulating images, means for displaying questions (referred to as emotion items) about the feeling elicited by the stimulating images that have been one by one shown on the image display apparatus as well as displaying the response to each question, means for gathering statistical data of the response to each emotion item with respect to the emotion elicited by each stimulating image, and processing means for evaluating psychotic manifestation and mental state based on the gathered statistical data. Wherein:

the database stores predetermined combinations of stimulating images photographed at different angles that have been selected from said stimulating images and plural emotion items that have been selected from said emotion items with respect to more than one psychotic manifestation and mental state, and the processing means collects the reaction value and the reaction-time value from the response to each emotion item that corresponds to each stimulating image, and also collects the reaction data and reaction-time data by comparing those values with reference values, and then collects attention data from the reaction data and the reaction-time data with respect to each stimulating image, thereby creating attention data in regard to a specific emotion item with respect to a specific stimulating image. Thereafter the processing means identifies a specific symptom based on the combination of the selected stimulating images and the emotion items comparing them with the stimulating image and emotion item stored in the database, and finally individual data is created for each specific symptom by including the comparison reaction data or/and reaction-time data of healthy subjects for a specific emotion item with respect to a specific symptom. Furthermore, the database stores three or more predetermined combinations, and individual data is provided for each of the three or more specific symptoms.

It is also possible to provide the above-mentioned psychotic manifestation and mental state evaluation method wherein when a specific symptom is discriminated, the evaluation is confirmed by using a discriminant that has been created in advance by reflecting both plus and minus values of attention data.

It is also possible to provide the above-mentioned psychotic manifestation and mental state evaluation method wherein said attention data with respect to specified stimulating image and specified emotion item has a three-dimensional structure in which plus values and minus values coexist.

Hereafter, embodiments of the present invention will be explained with reference to the drawings.

FIG. 1 is a block diagram of a psychotic manifestation and mental state evaluation apparatus 100 (expression cognition evaluation apparatus, mental disorder diagnostic support system) which is an embodiment of the present invention.

In FIG. 1, the psychotic manifestation and mental state evaluation apparatus 100 can, for example, be a personal computer comprising an input means 1, database 2 stored in memory, processing means 3, and a display image creation means 4. Each of the functions as will be described below could, for example, correspond to an instruction or code sections of a computer program executed by the processing means 3. The computer program can be stored in the memory or loaded in memory from a computer readable storage medium (e.g. CD-ROM, floppy disk, memory, etc.).

A combination selection input 6 in the drawing is inputted into the processing means 3 via the input means 1.

Figure 2:
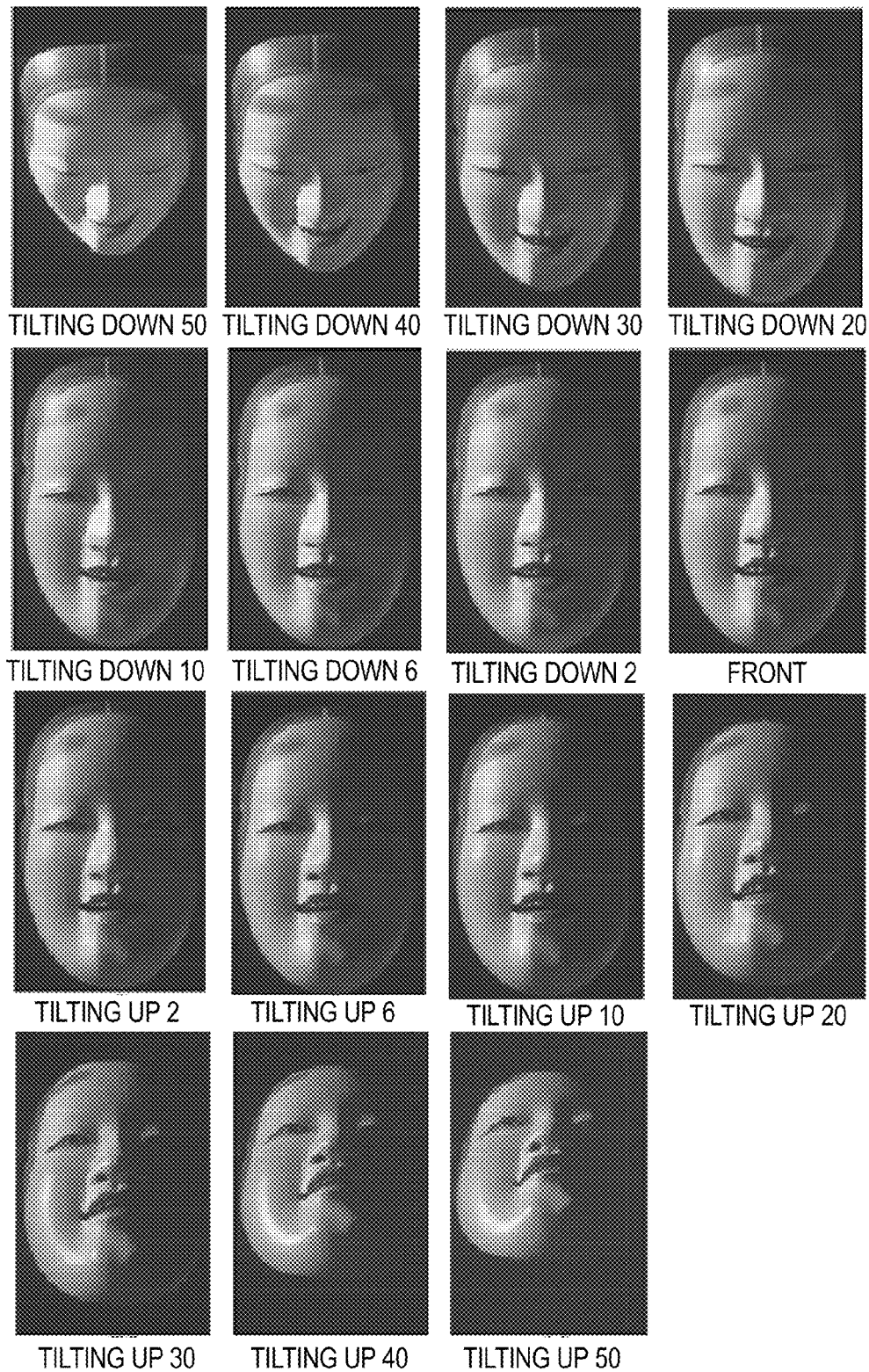
FIG. 2 shows stimulating Noh mask images photographed at different angles in the vertical directions.
Figure 3:
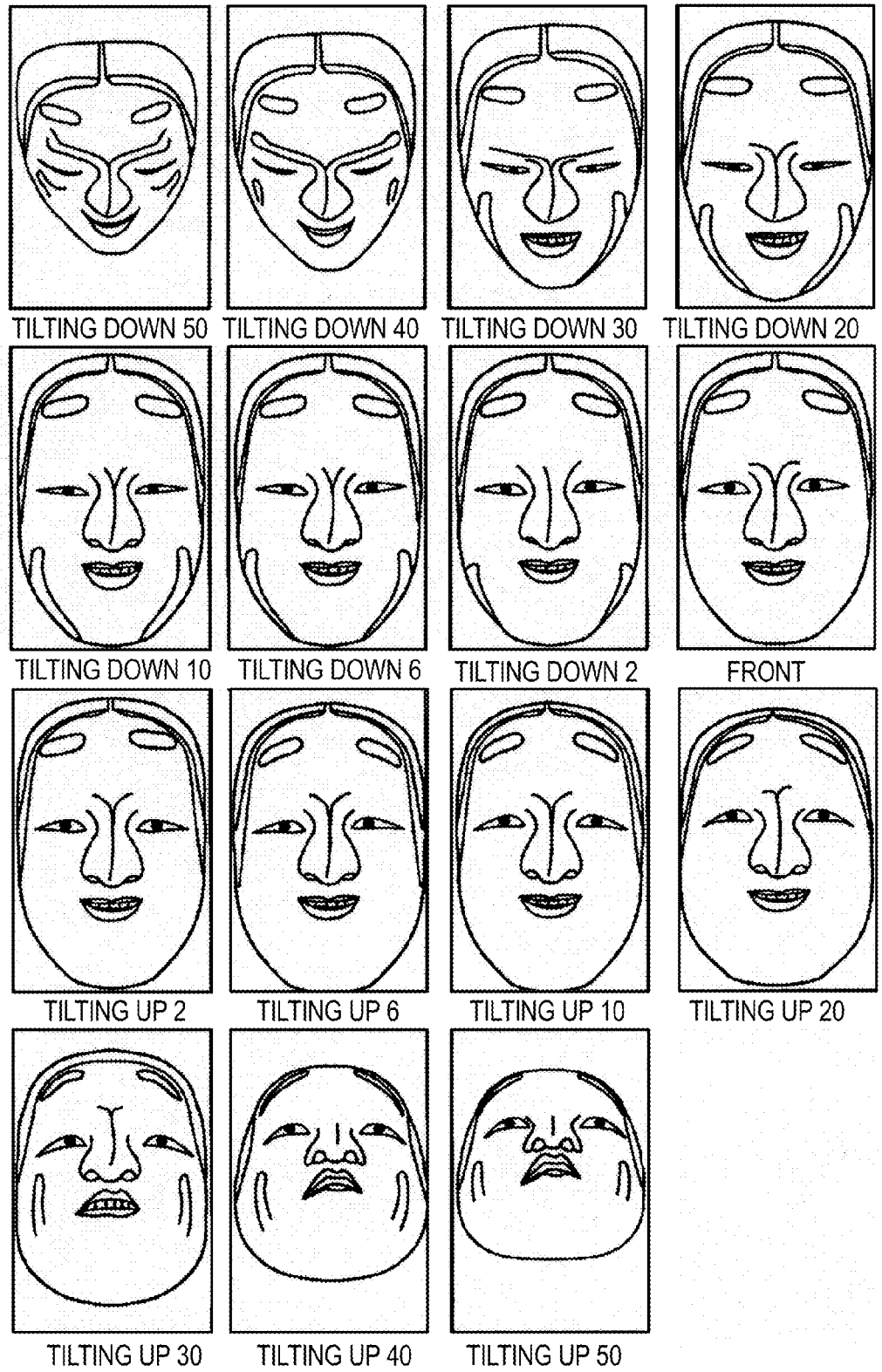
FIG. 3 shows line drawings of stimulating Noh mask images shown in FIG. 2.

Database 2 stores, for example, fifteen stimulating Noh mask images 21 shown in FIG. 2. The number of the images is not limited to fifteen and can be more than fifteen, or less than fifteen. Since FIG. 2 shows photo images and accordingly tend to become unclear in this application, an outline drawing that is regarded as FIG. 3 was created. Therefore, details of stimulating Noh mask images are evaluated with reference to FIG. 2 and FIG. 3.

As stated above, a Noh mask expresses various emotions by means of the angle of tilt in the vertical direction, thereby making the viewer perceive various emotions in response to a vertically tilting angle. Emotions include happiness, surprise, fear, sadness, hatred, anger, shyness, weirdness, absence of mind, and calmness. Herein, the first six emotions are regarded as basic emotions, and others are considered as auxiliary emotions. Among human emotions that are supported by an enormous amount of expression cognition research including the one conducted by Ekman that has been carried out since the 1970s, six emotions (happiness, anger, hatred, interest, fear, sadness) which we are clearly aware of or feel in daily life and which are expressed on other people's faces and easily understood beyond cultural difference are regarded as basic emotions. Herein, interest means surprise. Database 2 stores data 1, data 2 and data 3. Database 2 also stores programs and information necessary for processing the computer as well as information necessary to be processed by a processing means 3.

Data 1 includes a large number of stimulating Noh mask images 21 photographed at different angles in the vertical direction from tilting up 50 degrees to tilting down 50 degrees. The tilting angles can be within the range from tilting up 40 degrees to tilting down 40 degrees. Other angle ranges can also be made available.

Data 2 includes a large number of combinations 24 of more than one emotion 22 selected from the basic emotions and auxiliary emotions with more than one angle image 23 selected from stimulating Noh mask images.

According to those combinations, and as shown in selective combination 25 of FIG. 1, organic brain damage 26, schizophrenia 27, depressive tendency (including depression) 28, personality disorder, alcohol dependence, drug addiction, or PTSD, etc. can be discriminated as stated later on this document. FIG. 1 shows three symptoms: organic brain damage as option 1, schizophrenia as option 2, and depressive tendency (including depression) as option 3. However, symptoms are not intended to be limited to those above.

It is commonly known that patients with organic brain damage generally have considerable disorders of the cognition function, and a large amount of research on the relationship between the organic brain damage and the expression cognition has been carried out, and the link between ambiguous expressions and the functions of different brain regions is becoming certain. Organic brain damage causes a conspicuous cognitive deficit even regarding matters that threaten life. For example, if a person approaches somebody without recognizing somebody's "angry" emotion, there is a possibility that the person's life may be threatened. The inventors of this application focused on such characteristics of patients with organic brain damage. In addition to the inability to recognize an "angry" emotion, it is known that the superiority of a "happy" expression, which is readily recognized in ordinary people, does not work for a person with organic brain damage. Among studies of expressions, the superiority of a "happy" expression, which has been discovered based on a large number of studies of healthy subjects, means that a face which expresses happiness is easily memorized, difficult to forget, and easily recognized in comparison with other expressions; consequently, the rate of correct answer is considerably higher than other emotional expressions in the experiments of expression evaluation and the reaction time is shorter than other expressions. This knowledge has been applied to the Noh mask test.

Figure 4:
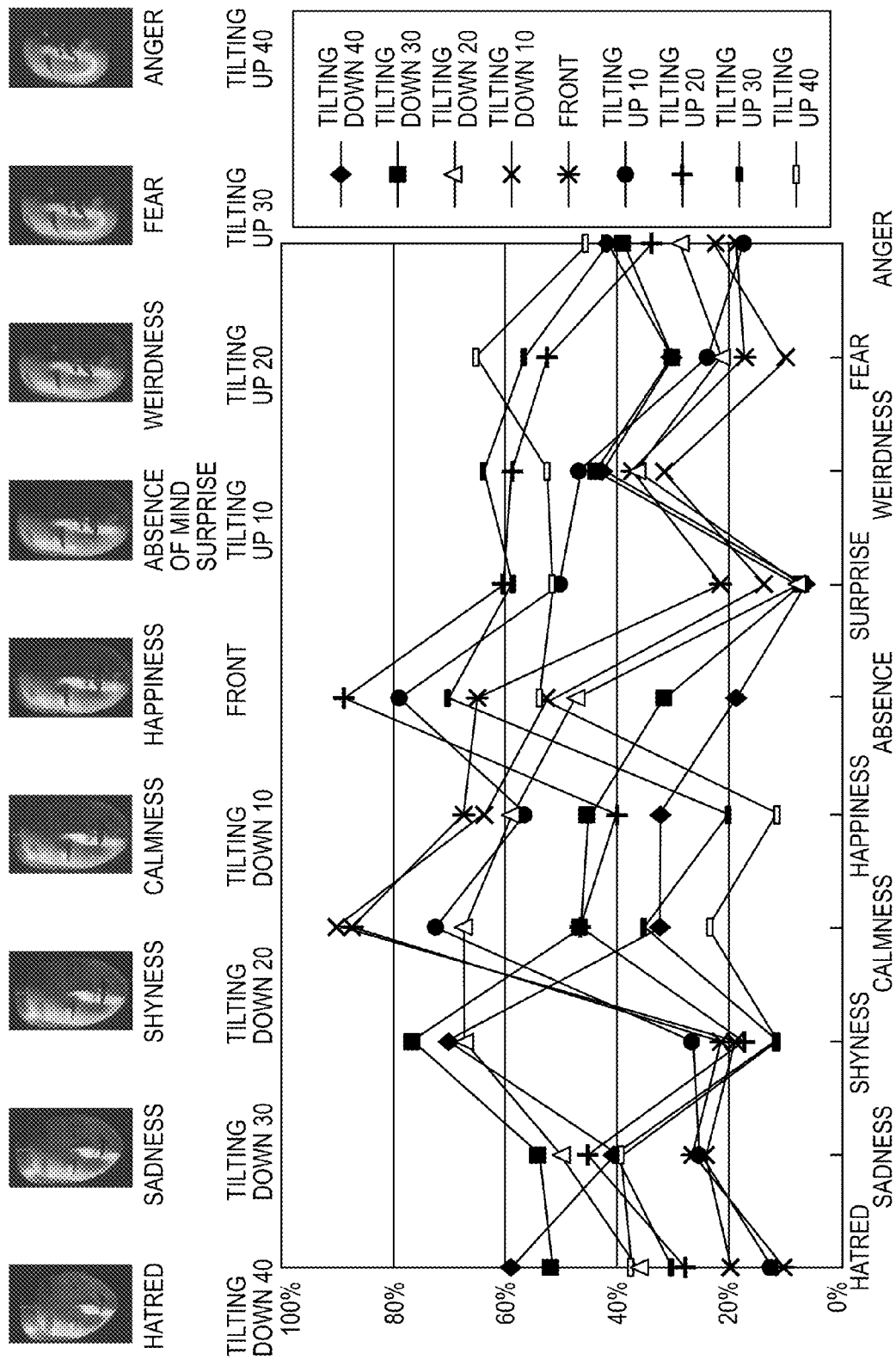
FIG. 4 shows data that has been stored in the database as data 3.

Data on healthy subjects is inputted into database 2 as data 3. FIG. 4 shows cognition results of healthy subjects with respect to stimulating Noh mask images. Healthy subjects tend to recognize Noh mask images photographed at angles between the range from slight downward angle to horizontal as pleasant stimulations, and Noh mask images photographed at very low or high angles are recognized as unpleasant stimulations.

"Schizophrenic patient"

Major schizophrenic symptoms described in DSM-IV (psychiatric diagnosis manual) are as follows:

A. Characteristic Symptoms

There are two (or more) of the following symptoms; each symptom always exists for a month (shorter when medical treatment is successful):

(1) Delusion (2) hallucination (3) disorganized conversation (example: frequently losing the plot or incoherence of thought) (4) considerably disorganized or catatonic behavior (5) negative symptoms, such as flattened emotion, poverty of thought, or lack of motivation.

Note: If delusion is bizarre, auditory hallucination explains the person's behavior one by one, or two or more voices seem to be talking to each other; only one of the symptoms in reference A is necessary.

B. Deterioration of Social or Vocational Function

For the most of the time period since the disorder started, one or more functions with respect to occupation, human relations, and self-supervision drastically deteriorate when compared to the level that person had attained before the disorder started (or, if disorder started during childhood or adolescence, it is impossible for that person to attain appropriate human-relational, academic, and vocational levels that are socially expected.)

Although schizophrenic symptoms have diversified characteristics according to the clinical entity (paranoid type, disorganized, catatonic, residual), common underlying conditions include cognitive deficit and thought disorder.

There are various studies of cognitive deficiency in schizophrenia, however, there is a consensus in that schizophrenic patients are poor at recognizing something ambiguous but can recognize something clear almost as good as healthy subjects do. The inventors of this application observed the situation where a schizophrenic patient, living in a hospital or a social rehabilitation facility, was confused by ambiguous instructions, such as "Please roughly do this" or "See if it is all right", causing relationships with its family to aggravate, and as a result, symptoms got worse. Therefore, we advise staff and family members to issue clear instructions and respond clearly.

Such "weak ability to cope with ambiguity" of schizophrenic patients also appears in expression cognition. Those patients can clearly recognize emotions when clear basic expressions are shown, however, they are easily confused by subtle and complicated expressions or emotions. For example, with respect to a "weird" emotion, a schizophrenic patient may feel that the other person is weird and consider that the person is an enemy. Thus, due to a "weak ability to cope with ambiguity", when schizophrenic patients encounter ambiguous expressions and stimulations, a leap in logic occurs thereby tending to increase delusion (thought disorder).

As stated above, it is possible for the Noh mask test to accurately detect such "weak ability to cope with ambiguity" in schizophrenic patients. To date there have been no methods established that use "subtle" and "ambiguous" expression stimulations like Noh mask images, basic, compound or complicated emotions, and emotions specifically peculiar to schizophrenia such as "weirdness."

(2-2) "Depressed Patient"

Depression

Major depression symptoms described in DSM-IV (psychiatric diagnosis manual) are as follows

[Great Depression Episode]

Five or more symptoms of the following symptoms coexist during the same two weeks, and mental functions have changed since symptoms started; and one of those symptoms is (1) depressed mood or (2) lost interest or joy.

1. Depressed mood almost all day, almost every day.
2. Considerable diminution of interest and joy in all of or most of activities almost all day, almost every day.
3. Considerable weight loss or weight increase without executing dietetic treatment (for example, change in weight by 5% or more a month), or decrease or increase in appetite almost every day.
4. Difficulty in sleeping or excess sleeping almost every day.
5. Psychomotor irritation or restraint almost every day.
6. Fatigability or diminution of vigor almost every day.
7. Feeling of worthlessness or excess or improper guilt feeling (sometimes delusive), (not simple self-reproachful mood or guilty conscience because of illness) almost every day.
8. Diminution of thinking power or concentration power, or presence of difficulty of making a decision almost every day.
9. Repetitive thought of death (not only fear of death), repetitive consideration of suicide in spite of no specific plans, suicide intention, or concrete plan for suicide.

Thus, various studies of the above symptoms underlying depression point out negative distortion of cognition.

When conducting a clinical examination of depressed people, the inventors have been trying to painstakingly correct the negative cognition with medication treatment. Furthermore, unlike other patients with mental disorders, most depressed patients have emotions and sympathism that are understandable in accordance with normal psychology. Therefore, when compared with healthy subjects, it is presumed that depressed people's circular ring structure of expression cognition does not change although their basic judgmental criteria will be negatively distorted when recognizing basic emotions as well as subtle and complicated emotions in the cognition of emotions and expressions.

From an input means 1, questions about emotions, that is, emotion items 11 are inputted as input data. A processing means 3 executes selection input 6 of necessary combinations chosen from database 2.

The Noh mask tests are carried out in the above-mentioned circumstances.

A processing means 3, as illustrated in FIG. 1, comprises an overall statistical data collecting means 31, an attention data collecting means 32, a specific symptom discrimination (extraction) means 33, an individual data creation and confirmation means 34, and a result output means 35.

The following advantages exist when asking patients to evaluate emotion items, such as basic emotions and other compound emotions or special emotions peculiar to schizophrenia including "weirdness," by using Noh mask stimulating images that create "subtle" and "ambiguous" expressions: that is, people with organic brain damage have a cognitive deficit with regard to the basic emotions, and schizophrenic patients have low scores with regard to items of "weirdness" and "shyness."

As stated above, by using basic emotions, it is possible to discriminate between organic brain disorder in which cognition of basic emotions is impossible and schizophrenia in which basic emotions can be recognized. Furthermore, the use of basic emotions makes it possible to detect personality of healthy subjects, characteristics of human relations, degree of work adjustment, vocational aptitude, and prediction of business results in addition to detecting a patient's mental state.

Stimulating Noh mask images used for a selected combination are ready for the display on the screen. Emotion items that are used in combination with the stimulating images are made selectable. All of the predetermined emotion items can be combined. In this case, data on necessary emotion items is selected when it is processed.

Thus, database 2 stores plural, such as three or more, predetermined combinations of stimulating images photographed at plural angles selected from stimulating image data as well as plural emotion items selected from emotion-item data with regard to the stimulating images for each human psychotic manifestation and mental state. Furthermore, the processing means 3 can select one combination of specific symptoms from a large number of preset combinations and can input a stimulating image and additionally an emotion item that corresponds to the stimulating image with regard to the selected combination. Also with regard to each emotion item, data on questions (YES, NO), affirmative responses (YES) and reaction-time value, which is the time period from when stimulation is first administered until a patient responds, are collected.

An overall statistical data collecting means 31, as shown in FIG. 1, is a function to conduct Noh mask tests and comprises a means 311 for inputting questions and responses to each emotion item that corresponds to each stimulating image, a means 312 for collecting reaction value and reaction-time value, and a means 313 for collecting reaction data and reaction-time data that corresponds to reference value.

Response data which is the basis of this embodiment comprises affirmative response data (1, 0 data showing "YES" or "NO") and reaction time data. And (1) the number of affirmative responses, (2) the number of expression evaluation variations, (3) balance coefficient of expression, and (4) deviation score from healthy subjects' reference data that have been obtained by recalculating affirmative responses for each emotion item are primary treated variables.

Now, reaction value and data for each stimulating image will be explained.

In FIG. 4, i denotes item number, j denotes photograph number, and k denotes examinee number. Reaction (R (i,j,k)) to stimulation was quantified by assigning a value of 1 to a "YES" response and a value of 0 to a "NO" response.—
Definition 1: If examinee k who looked at stimulating image (j) responded "YES" to item i, R (i,j,k)=1 is established, and if he/she responded "NO", R (i,j,k)=0 is established. (Example: if examinee No. 3 who looked at Noh mask image No. 5 and responded "YES" to "happy" which is emotion item No. 1, R (1,5,3)=1 is established.) R (i,j,k) of the healthy subject group is regarded as Rc (i,j,k).

15

Average reaction of healthy subjects can be expressed by (ΣRc (i,j,k)/15).

k=1

The number of affirmative responses to each item

The number of affirmative responses is defined as follows:

Herein, i denotes item number, j denotes photograph number, and k denotes examinee number.

The number of affirmative responses (L (i,k)) to each item is the number of "YES" responses to each item.

(The number of "YES" responses of examinee <k> to item <i>)

This relation can be expressed by the following equation:

$$L(i,k) = \Sigma R(i,j,k)$$  Equation 1 j=1

L (ik) of the healthy subject group is regarded as Lc (ik).

15

The number of average affirmative responses of a healthy subject to each item is expressed by (ΣLc (i,k)/15).

k=1

Reaction data is specified according to a degree of reaction value when compared to a reference value. In addition to the reaction value (or reaction time solely), reaction time is collected in the same manner as mentioned above, and reaction-time data is specified according to the length of reaction time when compared to a reference value.

An attention data collecting means 32, as illustrated in FIG. 1, comprises a means 321 for collecting attention data with respect to each stimulating image and a means 322 for identifying an emotion item focused upon with respect to a selected stimulating image, that is, a function for creating attention data of a specific stimulating image and a specific emotion item.

Examples of attention data of a specific stimulating image and a specific emotion item are shown in FIGS. 6 through 9 and 10. FIG. 10 summarizes the contents shown in FIGS. 6 through 9.

Figures 5, 6:
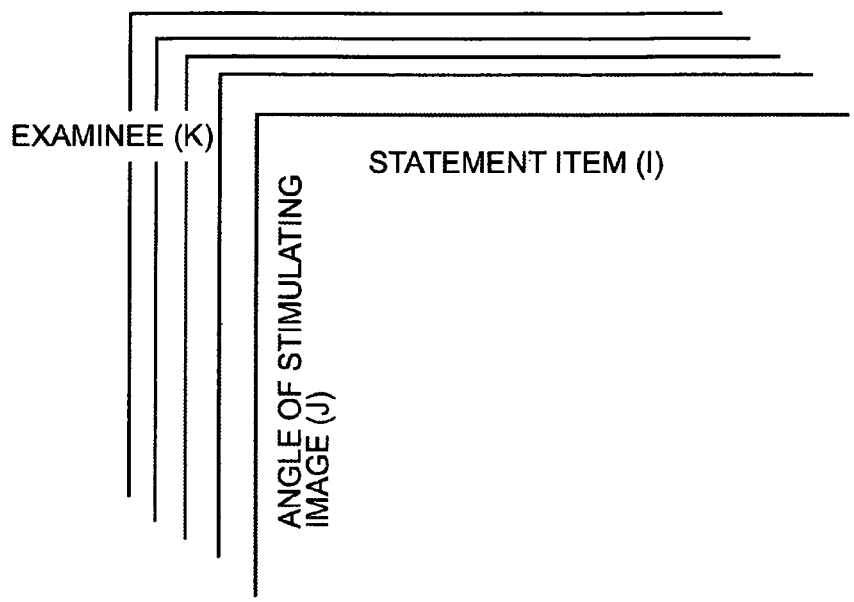
FIG. 5 explains how to gather statistical data for each stimulating image.
FIG. 6 shows attention data with respect to healthy subjects.

In those drawings, the horizontal fields show types of stimulating images and the vertical columns show emotion items. In the case of healthy subjects, as FIG. 6 shows, data on the reaction to each stimulating image is expressed by plus (+) for each emotion item.

On the contrary, in the case of organic brain damage, emotion item "happy" tends to be expressed by minus (–) when Noh images photographed at an upward angle of 30 degrees and 40 degrees were shown, and depressive emotion item "angry" tends to be expressed as plus (+) when Noh images photographed at a downward angle of 40 degrees and 30 degrees were shown. These tendencies can be recognized as prominent differences in comparison with FIG. 6.

In the case of schizophrenia, emotion item "hate" tends to be expressed as plus when a Noh image photographed at an upward angle of 10 degrees was shown and also expressed as minus when a Noh image photographed at an upward angle of 40 degrees was shown. Another emotion item "shy" tends to be expressed as minus when a Noh image photographed from the front (0 degrees) was shown. These tendencies can be recognized as prominent differences in comparison with FIG. 6.

In the case of people with depressive tendency (including depressed people), emotion item "hate" tends to be expressed as plus when Noh images photographed at a downward angle of 20 degrees and at an upward angle of 10 degrees were shown. Furthermore, emotion item "sad" tends to be expressed as plus when a Noh image photographed at a downward angle of 10 degrees was shown, and another emotion item "happy" tends to be expressed as minus when Noh images photographed from the front (0 degrees) and also at an upward angle of 10 degrees were shown. These tendencies can be recognized as prominent differences in comparison with FIG. 5. Besides the plus or minus indication shown in FIGS. 7 through 9, minor tendencies that indicate plus or minus can be added to the attention data.

FIG. 10 summarizes the results shown in FIGS. 6 through 9. By calculating attention data from the collected overall statistical data, it is possible to easily discriminate among organic brain damage, schizophrenia and depressive tendency (including depression), and the comparison of the obtained data with healthy subjects' attention data makes the obtained data more accurate.

With respect to the identified stimulating image and the identified emotion item, attention data has a two-dimensional structure in which plus-side data and minus-side data coexist. Furthermore, since some attention data is strong and some is weak, the two-dimensional structure appears as both a convex shape and a concave shape toward the plus side and the minus side, respectively, in the comparison with the reference value.

The attention data can be displayed on the display screen creation means 4, described later in this document, where the data is indicated as organic brain damage, schizophrenia, or depressive tendency (including depression). And, without those disease names, by displaying attention data about each emotion item corresponding to a stimulating image, it is possible to obtain the same effect as the indication of organic brain damage, schizophrenia, or depressive tendency (including depression).

Thus, the specific symptom discrimination means 33, as illustrated in FIG. 1, can output identified data relating to organic brain damage 331, schizophrenia 332, or depressive tendency (including depression) 333 and display data.

An individual data creation and confirmation means 34, as illustrated in FIG. 1, creates individual data of each identified symptom and provides data for evaluation and confirmation. This means 34 comprises an input means 341 for inputting healthy subject data for each diagnosis which means a fetch-in function, a cognitive mapping data creation means 342, a radar chart data creation means 343, a healthy subject data comparison means 345, and a means for applying discriminants (1), (2) and (3). Individual data for each diagnosis created by those means is displayed on the display screen creation means 4. Thus, the individual data creation and confirmation means 34 functions to evaluate and confirm the diagnosis.

A result output means 35, as shown in FIG. 1, comprises an output means 351 for outputting a comparison chart that compares data with the healthy subject data chart and an output means 352 for outputting a result data chart obtained by discriminants (1), (2) and (3). Those charts are displayed on the display screen creation means 4, as shown in FIG. 1. The display screen creation means 4 comprises a means 411 for displaying attention data of a specific stimulating image and specific emotion item, a means 412 for displaying a comparison chart that compares data with the healthy subject data chart, and a means 413 for displaying a result data chart obtained by discriminants (1), (2) and (3).

Discrimination by reaction time

Discrimination by reaction time is carried out in the same manner as discrimination by response.

Schizophrenic patients have a particular feeling described as "weirdness" throughout the period that starts from the beginning of symptoms and continues up to the chronic stage. By giving those schizophrenic patients a Noh mask test, asking them to evaluate whether the Noh mask's expression is "weird," and measuring the reaction time, it is possible to indicate their chronically preparatory state for feeling "weird." When compared with the data of healthy subjects, the time for schizophrenic patients to respond to all of the items is longer, 2800 ms or more, whereas the time for them to respond to the question "I think the Noh mask that is shown is weird" is 1200 ms or less only with respect to one of the Noh mask images tilting down at an angle of 10 degrees, front, tilting up at an angle of 10 degrees and 20 degrees.

A number of experiments regarding expression cognition of depressed people have been carried out, and most of them are focused on only reaction to negative emotions. Reaction values and reaction-time values are measured with respect to Noh mask images, compared with each reference value, and then attention data is collected about negative emotion items (minus) and positive emotion items (plus).

Since conventional depression evaluation systems conduct evaluation by means of a method, such as a questionnaire method, that is easily derived by an examinee, it is possible for the examinee to hide their disorders at school or in the work environment. According to a method of this embodiment, emotion items and Noh mask images are shown at random, which makes an examinee's manipulation almost impossible. Since an examinee's manipulation by learning is almost impossible, this method is an appropriate and reliable method to discriminate mood disorder (depressive tendency) the mood fluctuations of which needs to be continuously measured, and this method also functions as appropriate and reliable psychological testing that can be conducted periodically.

This time, by using the knowledge that depressed people tend to affirm negative emotions with respect to Noh mask images and their reaction time is short, the discrimination of people with depressive tendency (including depressed people) is carried out. Since the discrimination rate of the diagnosis system that uses reaction only is 90%, by applying the reaction time to the discriminant, it is possible to increase the discrimination rate up to a level of 95% or more.

Moreover, by using reaction-time data, it may be possible to detect the hypersensitive state of people suffering from PTSD or people with other anxiety disorders.

In many depression check lists (depression scales), it has been impossible to identify whether a people with depressive tendency is "showing depression", "resulting from personality disorder", "showing a part of schizophrenic symptoms", "associated with PTSD", "showing a part of anxiety disorders", or "a healthy subject is temporarily depressed."

In this embodiment, by using reaction time together with reaction itself and to some extent excluding other illnesses, it is possible to assist diagnosing depression and depressive tendency.

Filtering of a sub-clinical group (mental deterioration group)

Filtering is conducted based on reaction time (value) that has been so far obtained in many studies. In the case of healthy subjects, the average reaction time for all of the items is 1,600 ms, while in the case of a sub-clinical group (people whose mental well-being is slightly deteriorating including mentally disordered people and people with depressive tendency), the average reaction time is 400 ms or less, or 2,800 ms or more.

Filtering of schizophrenic patients:

Among tested people whose average reaction time for all of the items is 2,800 ms or more, a person whose average reaction time for the statement, "The Noh mask is weird," with respect to at least one of those Noh mask images that are tilting down at an angle of 10 degrees, straight ahead (front), tilting up at an angle of 10 degrees and 20 degrees is 1,200 ms or less is suspected to be schizophrenic. (If reaction time for other negative emotion items is also short, check to see if the person has depressive tendency (including depression) by examining the items stated below. Even when only the reaction time for the response to "weirdness" is short, if the reaction time for all of the images is short, feigned illness (pretending to be mentally disordered in a mental competency evaluation so as to avoid a criminal sentence) may be suspected).

Filtering of people with depressive tendency (including depressed people):

Among tested people whose average reaction time for all of the items is 2,800 ms or more, when the difference between the reaction time for negative emotion items (sadness, anger, hatred, weirdness, fear) and that for positive emotion items (happiness, shyness, calmness) is 1,000 ms or more and the reaction time for negative emotion items is short, depression (mental disease that requires outpatient medication treatment) is suspected. If the above difference is 500 ms or more and less than 1,000 ms, it is regarded that a healthy subject has depressive tendency (the person can function in a school or work environment providing that industrial or school counseling is made available to the person).

Emotion items, "surprise" and "absence of mind," that are linked with a level of arousal is considered to reflect hyperarousal of the PTSD symptoms.

For discrimination, application 346 of discriminants (1), (2) and (3) will be explained.

Three discriminants (1), (2) and (3) are shown below.

1) Discriminant for identifying organic brain damage (87% discrimination possible) among examinees who are suspected to be mentally ill according to Noh mask test results.

z=−0.550×Happiness tilting up 30−1.588×Happiness tilting up 40+0.972×Anger tilting down 40+0.999×Anger tilting down 30−0.276.

The attention data shown in FIG. 7 is applied to this equation.

2) Discriminant for identifying schizophrenia (82% discrimination possible) among examinees who are suspected to have mental disorders excluding people with organic brain damage. The higher the score becomes, the higher the possibility of schizophrenia.

z=−1.485×Hatred tilting up 40+1.330×Hatred tilting up 10−0.789×Shyness front+0.247

The attention data shown in FIG. 8 is applied to this equation.

3) Discriminant for extracting people with depressive tendency (90% discrimination possible) among a healthy subject group (companies, schools).

z=−0.295×Happiness front−1.420×Happiness tilting up 10+1.925×Sadness tilting down 10+1.137×Hatred tilting down 20+0.963×Hatred tilting up 10+0.408.

Figures 9, 21:
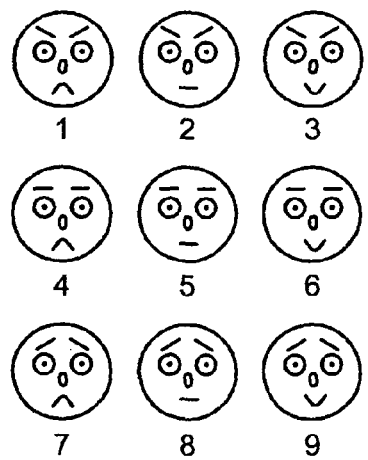
FIG. 9 shows attention data with respect to depressive tendency (including depression)
FIG. 21 shows an example of expressed emotions.

The attention data shown in FIG. 9 is applied to this equation. It is possible to increase the accuracy of discrimination by using a large number of stimulating images and emotion items.

The above-mentioned equation indicates that it is possible to detect the condition of illness or depressed state mentioned below based on knowledge and experiences according to differences of cognition of expressions indicated by stimulating Noh mask images. The above-mentioned equation can be further detailed.

When compared with healthy subjects, patients with organic brain damage do not feel happy with respect to the Noh mask images tilting up at an extreme tilting angle, and they tend to feel angry with respect to the Noh mask images tilting down at an extreme tilting angle. Accordingly, as one of the empirical rules, the above-mentioned discriminants have been obtained.

One of predominant symptoms that appear at the beginning of schizophrenia is delusion of persecution, and a common language that explains the delusion is "hatred". However, the psychiatric clinical experience indicates the characteristic in that chronic-stage schizophrenic patients cannot sense whether a person is trying to be deceptive and therefore, they tend to be easily cheated. This seems to be because schizophrenic patients are impervious to another person's malicious intent (publicly known research paper). Furthermore, a publicly known research paper indicates that schizophrenic people's cognition of the "shy" emotion indicated by the Noh mask has been distorted. For the above reasons, it is possible to adopt the above-mentioned discriminant (2) to discriminate schizophrenic people from healthy subjects by focusing on distortion in cognition of Noh mask images that is expressed as three emotional words: "weirdness," "hatred" and "shyness."

Although schizophrenic patients cannot recognize "hatred" from a Noh mask image tilting up at an extreme tilting angle (cannot notice other people's malicious intent), they feel hatred when they look at a Noh mask image tilting up at a slight tilting angle when compared to healthy subjects (a subtle sign induces them to become paranoid). Because the "shyness" cognition of schizophrenic patients is different from that of healthy subjects (publicly known research paper), they too frequently indicate the "shy" emotion with respect to a Noh mask image looking straight ahead (front).

As another example, detailed discriminants can be adopted.

Although healthy subjects consider the image of Noh mask looking straight ahead (front) to be "happy," depressed people tend to consider it to be "sad" or "hateful," which indicates cognition biased to negative emotions.

Figure 11:
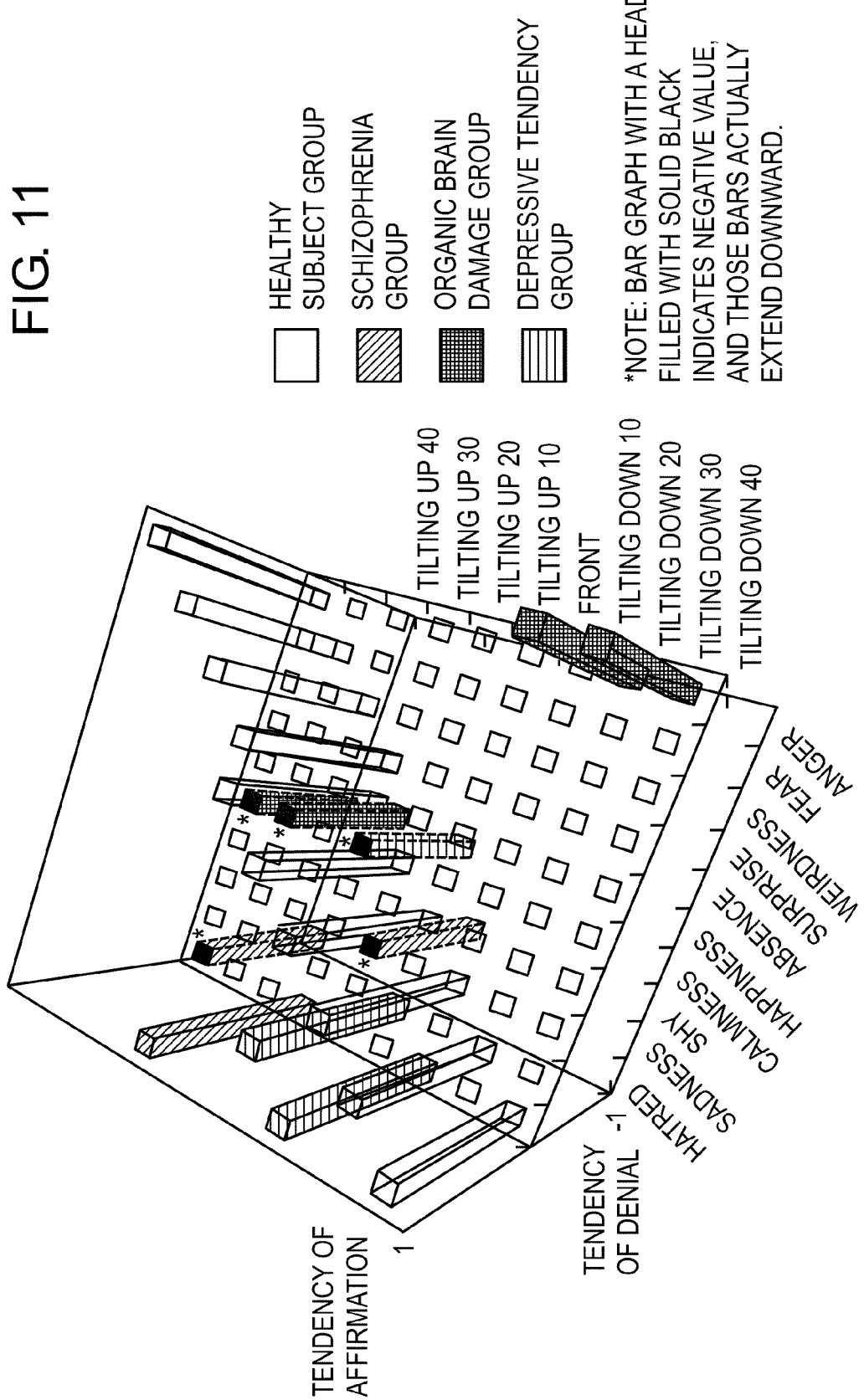
FIG. 11 illustrates the indicated conditions on the three-dimensional structure.
Figure 12:
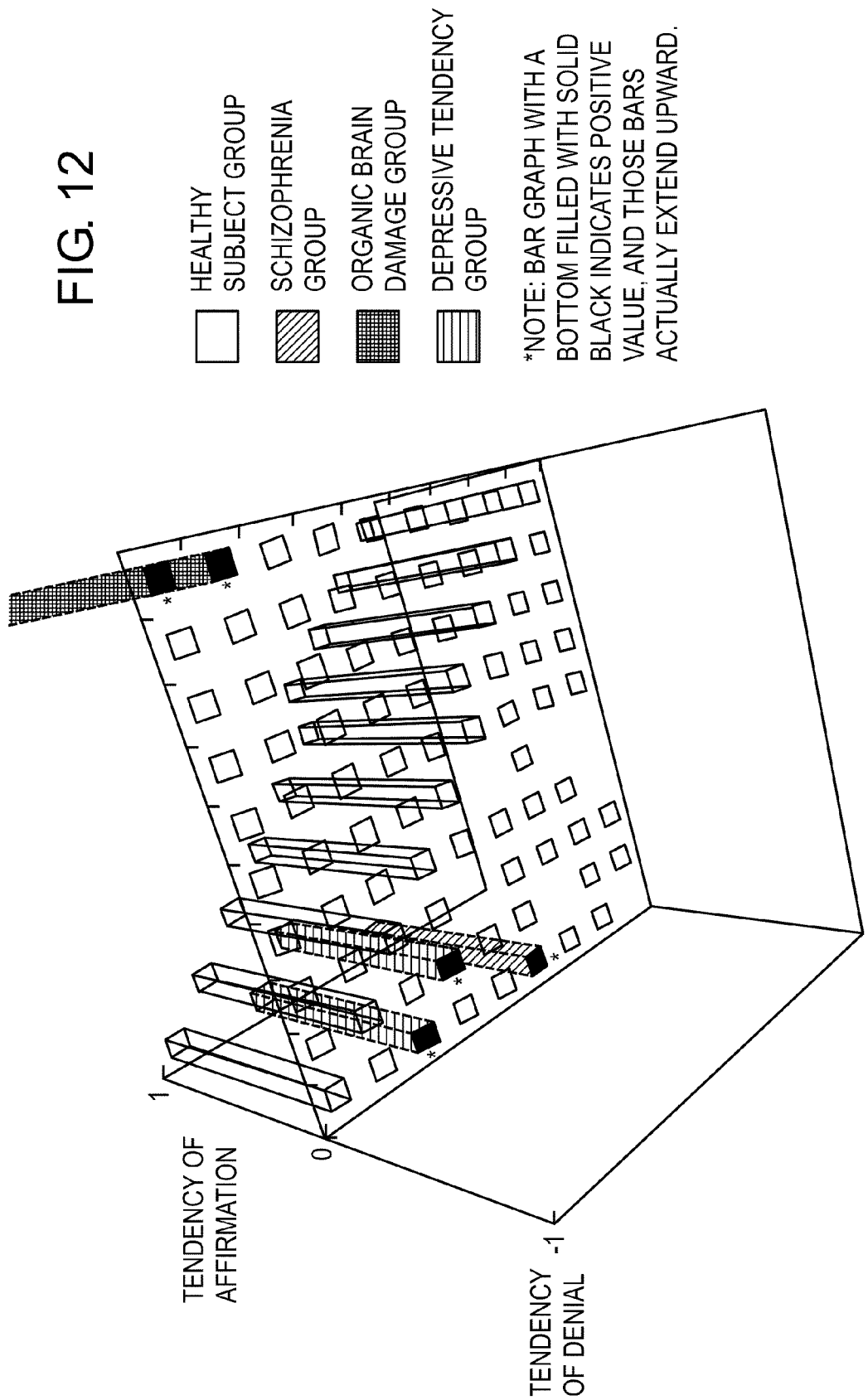
FIG. 12 specifically shows negative perspectives of the conditions indicated in FIG. 11.

FIG. 11 shows a positive perspective of three-dimensional structure which consists of three elements: type of disorder, stimulating image and emotion item. FIG. 12 shows a negative perspective of three-dimensional structure which is the same condition as shown in FIG. 11, and to facilitate visual understanding, the block graph on the positive side has been omitted (although the block graph of healthy subjects are shown).

Figure 13:
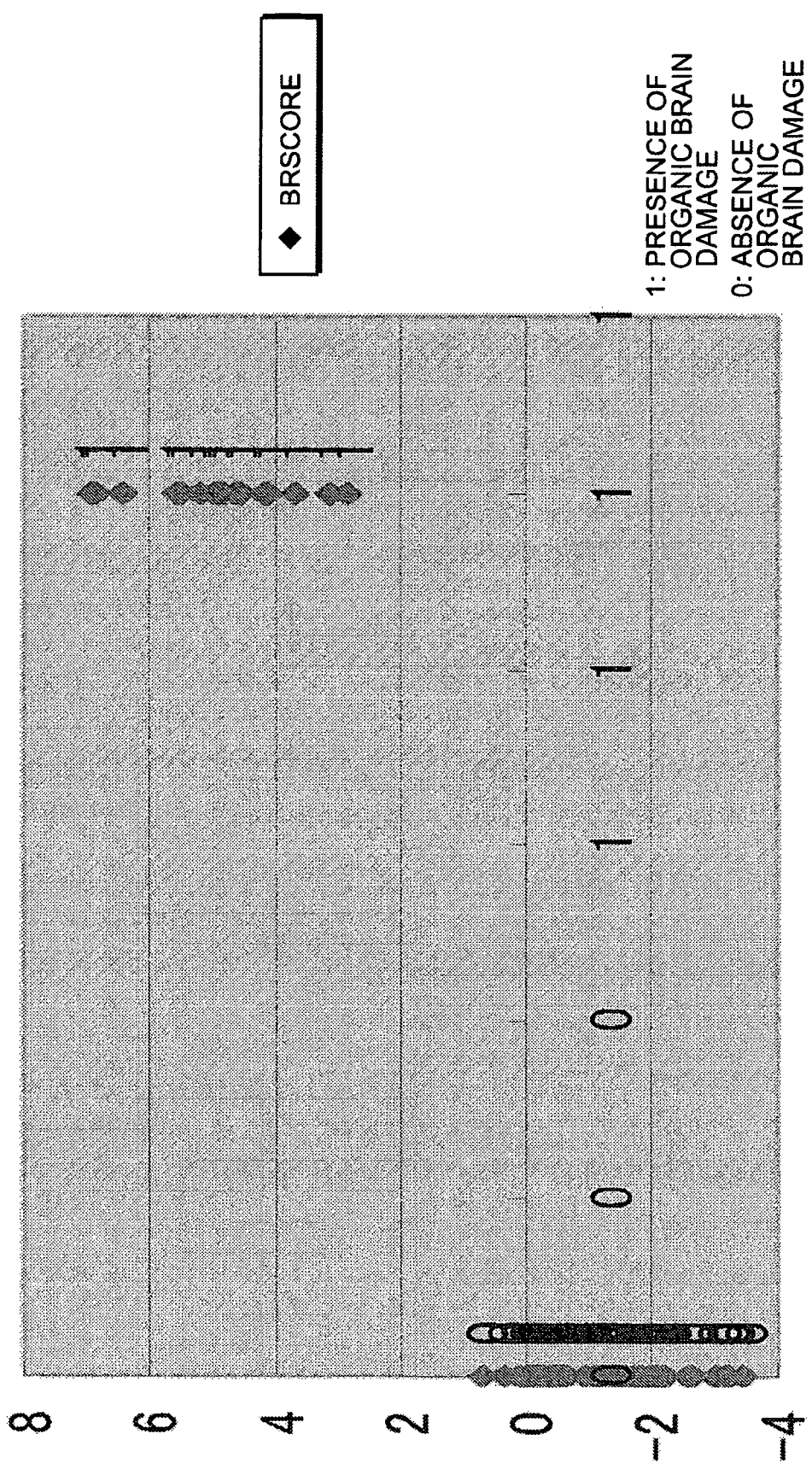
FIG. 13 shows the organic brain damage discrimination score (BRSCORE)

FIG. 13 shows the organic brain damage discrimination score (BRSCORE). As shown in FIG. 13, a group with organic brain damage and a group without organic brain damage are clearly separated.

Figure 14:
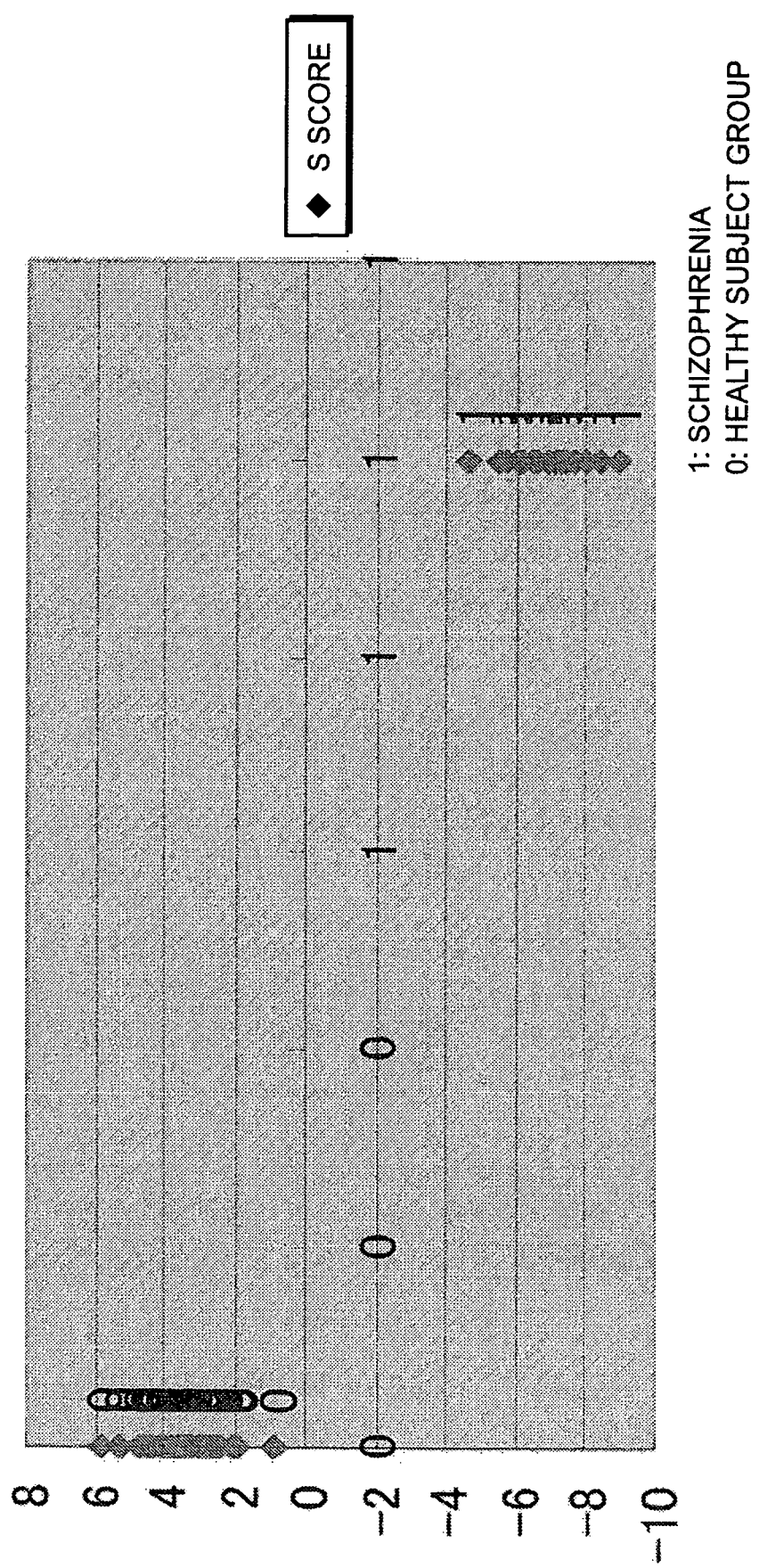
FIG. 14 shows the schizophrenia discrimination score (S score)

FIG. 14 shows the schizophrenia discrimination score (S score). A schizophrenia group and a healthy subject group are clearly separated as shown in FIG. 14.

When using discriminant (2) that uses a simple and quick method to shorten the time, the score increases as the possibility of schizophrenia increases. However, FIG. 12 is the situation in which the discriminant is introduced by using all of the variables to set the discrimination rate at 99%, and in this case, as a schizophrenic person's expression cognition characteristic becomes strong, the value decreases, and a schizophrenic patient's value is negative.

Figure 15:
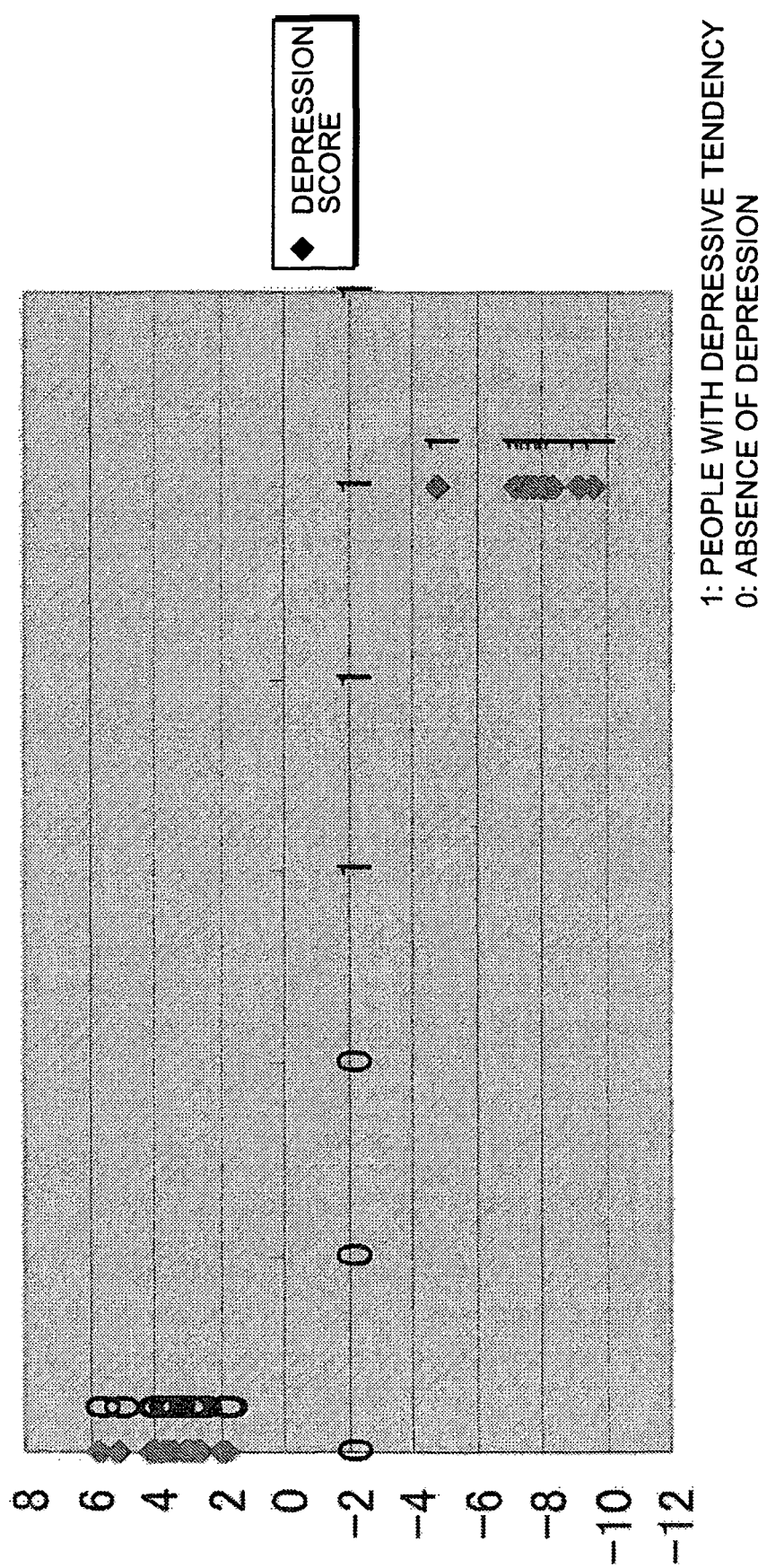
FIG. 15 shows the depressive tendency (including depression) discrimination score (depression score)

FIG. 15 shows depressive tendency discrimination score (depression score). A group of healthy subjects with depressive tendency and a group of people without depressive tendency are clearly separated as shown in FIG. 15.

As shown in FIGS. 13 through 15, the processing means 3 computes either negative or positive score when a coefficient is preset for each stimulating image for each combination and statistical data of healthy subjects is inputted, and it also computes a positive or negative score when statistical data of those who have specific symptoms is inputted.

The horizontal axis shows 0 for the comparison group (non-illness group) and 1 for the illness group.

Figure 16:
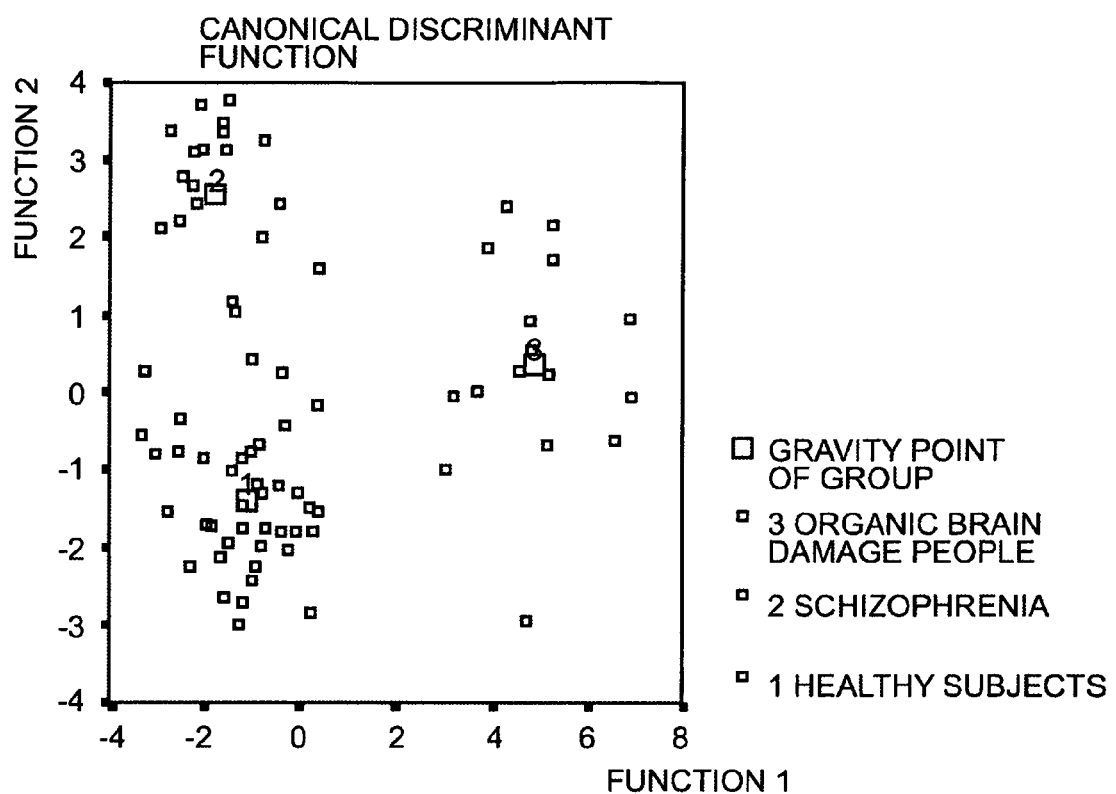
FIG. 16 shows the canonical discriminant function.

FIG. 16 shows the canonical discriminant function which statistically indicates three groups: healthy subject group, schizophrenia group and organic brain damage group. In FIG. 16, function 1 and function 2 are as follows:

Function 1: The degree of collapse of the circular ring structure of expression cognition (The value increases as the balance collapses in all directions).

Function 2: Bias of the circular ring structure of expression cognition toward "pleasant" side (The value increases as the axis of pleasant-unpleasant is undersized toward "pleasant" side. In the case of function 1, the balance collapses in all directions, but in the case of function 2, the circular ring structure collapses and becomes a semicircular structure).

As stated above, results are outputted.

As stated above, there are two discrimination methods: a statistical discrimination method and a discriminant discrimination method. The statistical discrimination method is to collect statistical data of affirmative responses to stimulating images and emotion items with respect to an inputted combination or of reaction time when a response to an emotion item about the stimulating image is made; to compute reaction data and reaction-time data by comparing data with reference value; and to compare those statistical data with reaction data on stimulating images and the relevant stimulating images with respect to the corresponding combination of healthy subjects and/or reaction-time data; and as a result, to be able to identify specific symptoms. The discriminant discrimination method compares the statistical value (score) of an emotion item in respect to stimulating image that indicates the characteristics of a specific symptom with statistical value (score) of healthy subjects.

The statistical discrimination method and the discriminant discrimination method can be used as parallel processing methods or as serial processing methods. The serial processing method is shown by the chained line or dot-dashed line in FIG. 1. The adoption of the serial processing method increases the discrimination probability. Furthermore, the simultaneous use of the discrimination by the number of affirmative responses and the discrimination by the reaction time also increases the discrimination probability.

Next, the display image creation means 4 will be explained.

Several profiles will be shown below.

FIG. 17 shows the expression structure model shown on a radar chart with respect to organic brain damage.

Figure 18:
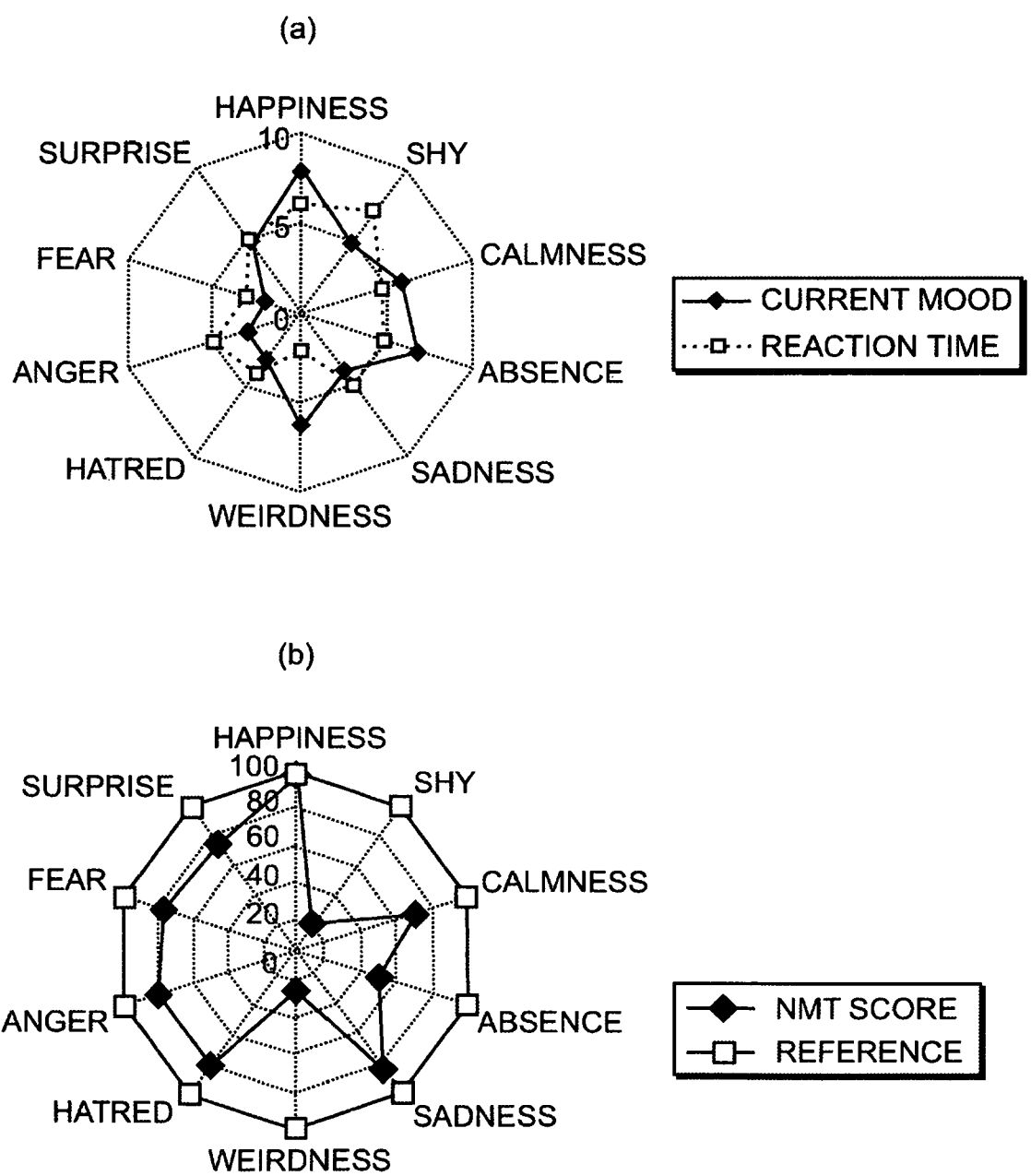
FIG. 18 shows the expression circular ring structure model with respect to schizophrenia.

FIG. 18 shows the expression structure model shown on a radar chart with respect to schizophrenia.

Figure 19:
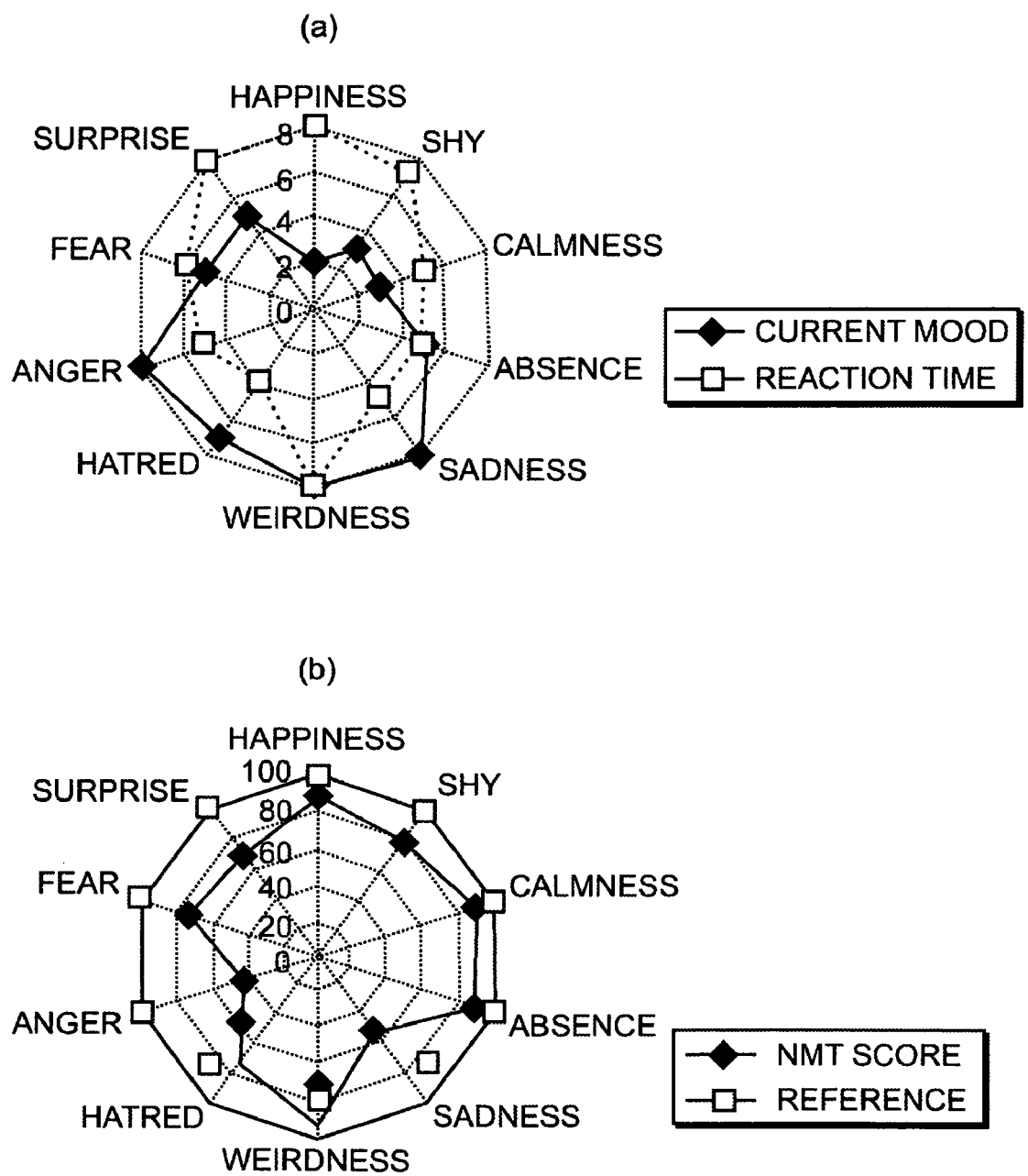
FIG. 19 shows the expression circular ring structure model with respect to depressive tendency (including depression) by means of a radar chart.
Figure 23:
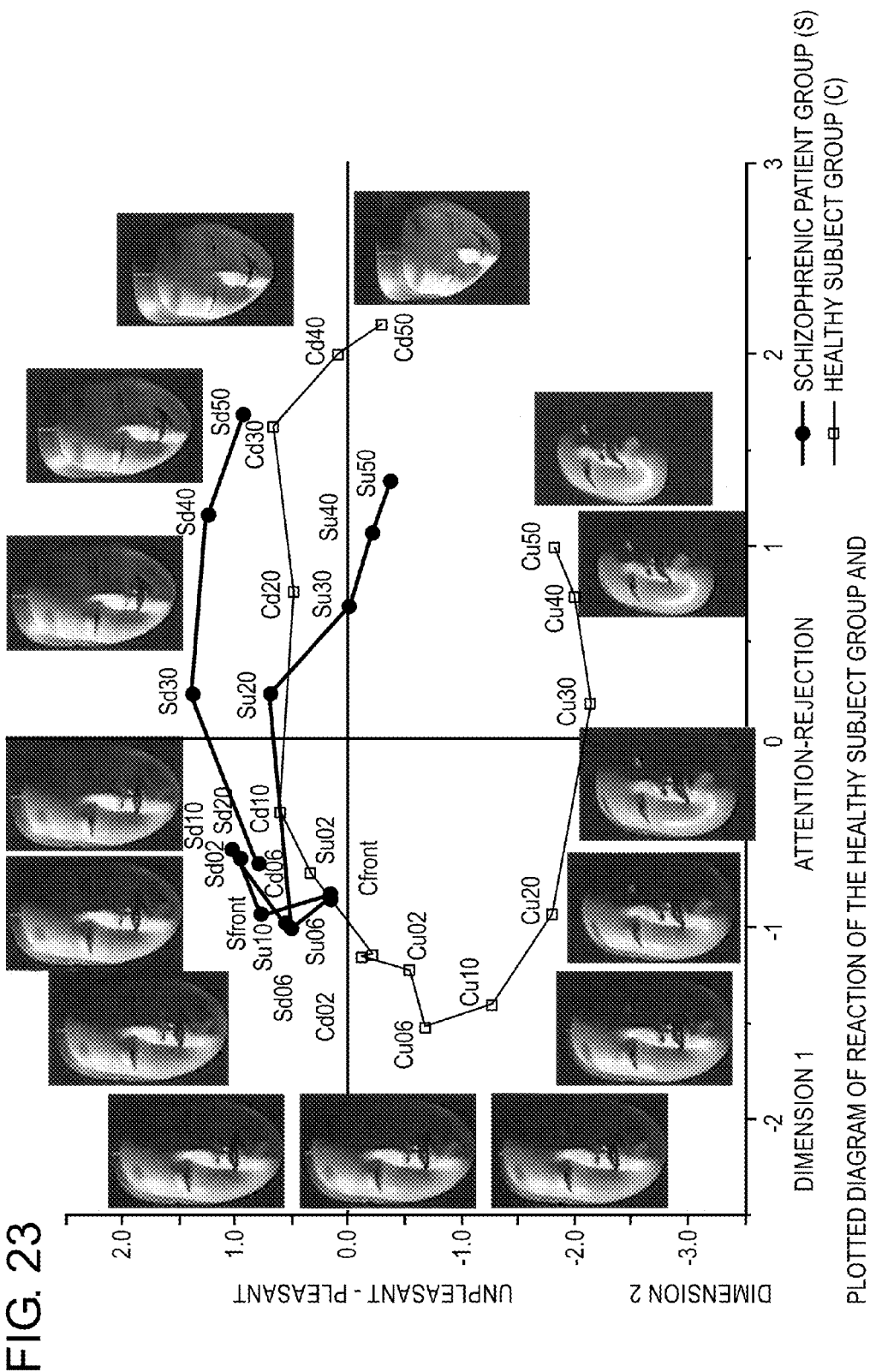
FIG. 23 shows an example of a publicly known two-dimensional drawing.

FIG. 19 shows the expression circular ring structure model shown on a radar chart with respect to depressive tendency (including depression).

Those drawings display statistical data of identified stimulating image for each identified emotion item as a profile and also display a profile of healthy subjects in contrast.

Variables indicated as "current mood" are the sum of the number of "YES" responses to emotion items such as "happiness" that is, the number of affirmative responses. (If "YES" is answered to all of nine Noh mask images, the value is 9).

The NMT score stands for Noh mask test score and is a standardized score so that "100 scores" means that the pattern of answers agrees with the pattern more than 70% of healthy subjects have answered, and "0 score" means that none of answers agrees with healthy subjects' answer pattern.

FIG. 17 shows the recognition pattern of organic brain damage.

As shown in FIG. 17(a), in the expression recognition pattern of patients with organic brain damage, the circular ring structure of "current mood" (the number of affirmative responses to emotion items) collapses because responses to emotion items that are supposed to be near and similar in healthy subjects are not similar, causing the balanced circle to break thereby resulting in an irregularly plotted graph. As a result, the area within the lines of the graph is very small.

FIG. 17(b) shows the ability to read other people's expression. As this drawing shows, NMT scores are also scattered. It is important to notice that among the basic emotions the scores of the most important expression ("happy," "angry," etc.) are low.

FIG. 18 shows the expression recognition pattern of schizophrenic patients.

As FIG. 18(a) shows, with respect to the expression recognition pattern of schizophrenic patients, in the "current mood" (the number of affirmative responses to emotion items), the circular ring structure of the number of affirmative responses to unpleasant emotions collapses (low score) creating a semicircular structure biased toward pleasant emotions because the ability to recognize unpleasant emotions which creates a circular ring structure in the healthy subject pattern is low. However, the average score of the "weird" emotion is exceptionally higher than the scores of healthy subjects (no significant difference).

FIG. 18(b) shows the ability to read other people's expression. As shown in this drawing, NMT scores of basic emotions are high in the same way as healthy subjects, whereas scores for complicated emotions including "shy" is low.

FIG. 19 shows the expression recognition pattern of people with depressive tendency (including depressed people).

As shown in FIG. 19(a), in the expression recognition pattern of people with depressive tendency (including depressed people), "current mood" (the number of affirmative responses to emotion items) has a circular ring structure (of radar chart) as is the case with healthy subjects, but the structure tends to be biased toward negative emotions.

FIG. 19(b) shows the ability to read other people's expression. As shown in this drawing, although NMT scores are basically the same as those of healthy subjects, negative emotions, such as "sadness", "anger" and "hatred," tend to be affirmed, thereby decreasing the total score.

FIG. 20 shows an example of vocational profile (application to a suitable vocation diagnosis system).

The variable titled "Expression that is apt to be most noticed" is "the number of Noh mask image evaluation changes," and the variable adds 1 to the score when different responses, such as "YES" and "NO", were made to adjacent Noh mask images that are among nine images photographed at different angles. For example, If the answers were "YES, NO, NO, NO, NO, YES, NO, NO, NO," 3 points are added to the score (since actual presentation is done at random, manipulation by an examinee is impossible). Emotion items with high scores are interpreted that evaluation of those emotions changes significantly, and the examinee is always conscious about those expressions and tends to focus those emotions when the examinee reads other people's expressions. Although a comparative study of this score with TEG (Todai-style egogram) and MINI-124 (the shortened version of MMPI which is a questionnaire-style simplified psychological test that is considered to have most diagnostic ability) has not been open to public, correlations between clinical scales and personality have been obtained (comorbid appropriateness).

FIG. 20(a) shows the expression recognition pattern of several skilled psychiatrists, which indicates the following common points: psychiatrists paid attention to first "calmness" and "absence of mind" because they may check for consciousness disorder at the time of usual clinical examination of patients, then the psychiatrists paid attention to "sadness."

FIG. 20(b) shows the expression recognition pattern of several skilled clinical psychotherapists, which indicates that they paid attention to "sadness." Such characteristics are common to medical and welfare workers who are not medical doctors, and a specific characteristic that is common to welfare workers is that they pay attention to other people's emotion and think to assist them.

FIG. 20(c) shows the expression recognition pattern of skilled sales representatives, which indicates that they paid attention to "happiness" and "surprise." It is presumed that they are always conscious about whether people are personable and happy to talk and also focus on whether a potential customer is being persuaded by the sales person's sales talk (surprised and happy to listen).

Furthermore, the inventors' research includes several studies of mothers and children who are involved in domestic violence (DV), which indicate that mothers who neglect children (nourishment rejection) have low expression cognition ability, while abused children have higher expression cognition ability than healthy subjects, and they also pay attention to "hateful" and "angry" expressions (the number of Noh mask image evaluation changes), which means that they always focus on whether they are disliked by other people or whether they may make somebody angry. Students who have been bullied at school show the same tendency, therefore, this method can be expected to be used as a clinical screening system at schools. Moreover, in the unreleased studies targeted at high school students and carried out by the inventors of this application, correlations between people who express an angry emotion and Noh mask test results were found; therefore, it is expected that this method may be applied to a mental health check system to take preventive measures against serious crimes caused by "children who suddenly become violent," which is a current problem, or by ordinary juveniles.

Thus, by recounting data obtained from Noh mask expression cognition experiments, this method can be used for a corporate human affairs support system, such as a personality check system, career choice support system, appropriate job posting, and prediction of business results in addition to medical diagnosis.

As an example of image display, a radar chart, which is an expression circular ring structure model (a publicly known model proposed by Schlosberg), is created by using data summed for each emotion item as an emotion score. It is considered that human emotions make up a circular ring structure (a famous psychological theory that says human emotions circulate from surprising→happy→sad→hateful→angry→fearful and return to surprising). Based on the model, to superimpose images on the circular ring structure, the emotions are displayed on the radar chart in sequential order of surprise, happiness, shyness, calmness, absence of mind, sadness, weirdness, hatred, anger, and fear. Computed results are printed by a display image output means (diagnosis aid means) including an attached printer for use by an examinee. Furthermore, the same results are also printed for use by an expert.

Created data is analyzed, and illustrations of a face are created, and based on the result data of the expression cognition experiment, "Your mood today" can be indicated by changing the expression of the illustration. For example, data can be outputted in the style such as "Degree of high spirit" (the rate of affirmation of "happiness"+the rate of affirmation of "surprise"×0.5 and "Degree of depression" (inverse values for plus and minus of discriminant 3). Results are outputted as average values by using morphing technology (visually averaging technique) according to the ratio of each expression. FIG. 20 shows an example of image display (expressed emotion display).

Furthermore, a profile of sample analysis is shown in FIG. 22. Example of both schizophrenic patients and people with depressive tendency (including depressed people) are displayed in FIG. 22. Each examinee's reaction results are analyzed by a multivariate analysis technique (example: MDS (multidimensional scaling), factor analysis, and Hayashi's quantification theory), and each Noh mask image is mapped in each examinee's cognitive space.

Specifically, data of reaction to plural emotion items with respect to each Noh mask image is counted for each angle of tilt of the Noh mask image. And, to conduct cognitive space mapping, images which have a similar reaction pattern are arranged close to each other and images which do not have similar reaction pattern are arranged far away by using the correlation coefficients and a degree of similarity as indexes. (When mapping images 1, 2 and 3; image 1 and image 2 that show an appropriate data matrix are mapped close to each other; and image 2 and image 3 that are not similar are mapped away from each other; thus, images 1 and 2 are visually away from image 3 and easily observed.)

At the same time, by estimating, from mapped Noh mask images, cognitive meaning of each orthogonal axis that creates cognitive space, it is possible to estimate a mechanism of how each examinee recognizes emotions indicated by Noh mask images. (For example, in this application, with regard to dimension 1 (x-axis), the emotion affirmation rate was examined with regard to positive high scores Cd50, Cd40, Sd50 and Cd30, and negative high scores Cu06, Cu10, Cu02 and Cd02, and it was found that the affirmation rate of "curse" was high among positive high score images, and that of "interest" was high among negative high score images. Accordingly, dimension 1 was named after "attention-rejection". With regard to dimension 2 (y-axis), the emotion affirmation rate was examined with regard to positive high scores Sd30, Sd40, Sd50 and Sd10 and negative high scores Cu30, Cu40, Cu50 and Cu20, and it was found out that the affirmation rate of "calmness," "hope" and "shyness" was high among positive high score images and the affirmation rate of "absence of mind," "surprise," "sadness" and "curse" was high among negative high score images. Accordingly, dimension 2 was named after "pleasant-unpleasant.")

Since spatial mapping of Noh mask images clearly shows that each mental illness has its own point of discrimination, to present the mapping to an expert can be an effective diagnosis aid tool. As a result, it is possible to reduce the time required for psychiatrists and experts to conduct diagnosis.

The results can be outputted on the screen or printed out on paper for use by an examinee or/and use by an expert as stated earlier in this document.

Thus, by collecting data for each symptom for which responses to emotion items with regard to stimulating Noh mask images have been preset, it is possible to automatically assist diagnosis of a large number of and at least plural symptoms of organic brain damage, schizophrenia and depressive tendency (including depression), thereby making it possible to help accurately and quickly diagnose a large number of patients multilaterally.

Specifically, it is possible to accurately and quickly diagnose a large number of patients for whether they have organic brain damage, are schizophrenic or depressed, and is also possible to accurately and quickly diagnose other symptoms. Furthermore, it is possible to utilize this method for a patient medical treatment support system as well as a system for self-evaluation of emotions.

While the invention has been described in terms of its preferred embodiments, it should be understood that numerous modifications may be made thereto without departing from the spirit and scope of the present invention. It is intended that all such modifications fall within the scope of the appended claims.

What is claimed is:

1. A psychotic manifestation and mental state evaluation apparatus comprising:
    a database which stores data of stimulating Noh mask images that express various kinds of human emotions according to changes of the angles at which the masks are photographed from tilting up to tilting down;
    an image display apparatus for displaying the stimulating images;
    means for displaying questions, referred to as emotion items, about the feeling elicited by the stimulating images that have been one by one shown on the image display apparatus as well as displaying a response from a subject being evaluated to each question based on response data which includes affirmative response data, reaction data and a reaction-time value;
    means for gathering statistical data of the response to each emotion item with respect to the emotion elicited by each stimulating image; and
    processing means for evaluating psychotic manifestation and mental state based on the gathered statistical data including the number of affirmative responses, a number of expression evaluation variations, a balance coefficient of expression and a deviation score from healthy subjects' reference data that have been obtained by recalculating affirmative responses from each emotion item,
    wherein said database stores predetermined combinations of stimulating images photographed at different angles that have been selected from said stimulating images and plural emotion items that have been selected from said emotion items with respect to more than one psychotic manifestation and mental state,
    wherein said processing means collects a reaction value and a reaction-time value from the response data of the response to each emotion item that corresponds to each stimulating image, collects reaction data by comparing the reaction and reaction-time values with reference values, and collects attention data based on the reaction data with respect to each stimulating image, and evaluating psychotic manifestation and mental state based on the collected data, thereby creating attention data in regard to a specific emotion item with respect to a specific stimulating image, wherein the attention data, when used, permits said psychotic manifestation to be easily discriminated, said psychotic manifestation being one of organic brain damage, schizophrenia and depressive tendency, wherein said attention data with respect to specified stimulating image and specified emotion item has a three-dimensional structure in which plus values and minus values coexist and is displayed on said image display apparatus to permit a visual understanding of the condition of the subject, wherein after the collection, said processing means identifies a specific symptom that corresponds to said psychotic manifestation based on the attention data and a result of comparing of the selected stimulating images and the emotion items to the stimulating image and emotion item stored in the database, and wherein individual data is created for each specific symptom by including a result of comparing the reaction data to the reaction data of healthy subjects for a specific emotion item with respect to a specific symptom.

2. A psychotic manifestation and mental state evaluation apparatus according to claim 1, wherein said individual data includes emotion item specified for specific stimulating image and reaction data on stimulating image for each emotion item.

3. A psychotic manifestation and mental state evaluation apparatus according to claim 1, wherein said database stores three or more predetermined combinations, and individual data is provided for each of said three or more predetermined combinations of symptoms.

4. A psychotic manifestation and mental state evaluation apparatus according to any one of claims 1 through 3, wherein when a specific symptom is discriminated, the evaluation is confirmed by using a discriminant that has been created in advance by reflecting plus value of attention data.

5. A psychotic manifestation and mental state evaluation apparatus according to claim 1, further comprising:

a display image creation means which displays a profile of said statistical data on stimulating image specified for said each specific emotion item and also displays a profile of healthy subjects for comparison.

6. A psychotic manifestation and mental state evaluation apparatus comprising:

a database which stores data of stimulating Noh mask images that express various kinds of human emotions according to changes of the angles at which the masks are photographed from the tilting up to tilting down;

an image display apparatus for displaying the stimulating images;

means for displaying questions, referred to as emotion items, about the feeling elicited by the stimulating images that have been one by one shown on the image display apparatus as well as displaying a response from a subject being evaluated to each question based on response data which includes affirmative response data, reaction data and a reaction-time value, means for gathering statistical data of the response to each emotion item with respect to the emotion elicited by each stimulating image, and processing means for evaluating psychotic manifestation and mental state based on the gathered statistical data including the number of affirmative responses, a number of expression evaluation variations, a balance coefficient of expression and a deviation score from healthy subjects' reference data that have been obtained by recalculating affirmative responses from each emotion item, wherein said database stores predetermined combinations of stimulating images photographed at different angles that have been selected from said stimulating images and plural emotion items that have been selected from said emotion items with respect to more than one psychotic manifestation and mental state, wherein said processing means collects a reaction value and a reaction-time value from the response data of the response to each emotion item that corresponds to each stimulating image, collects the reaction data and reaction-time data by comparing the reaction and the reaction-time values with reference values, and collects attention data based on the reaction data with respect to each stimulating image, and evaluating psychotic manifestation and mental state based on the collected data, thereby creating attention data in regard to a specific emotion item with respect to a specific stimulating image, wherein the attention data, when used, permits said psychotic manifestation to be easily discriminated, said psychotic manifestation being one of organic brain damage, schizophrenia and depressive tendency, wherein said attention data with respect to specified stimulating image and specified emotion item has a three-dimensional structure in which plus values and minus values coexist and is displayed on said image display apparatus to permit a visual understanding of the condition of the subject, wherein after the collection, said processing means identifies a specific symptom that corresponds to said psychotic manifestation based on the attention data and a result of comparing of the selected stimulating images and the emotion items to the stimulating image and emotion item stored in the database, wherein individual data is created for each specific symptom by including a result of comparing the reaction data to the reaction data of healthy subjects for a specific emotion item with respect to a specific symptom, wherein said processing means includes individual data creation and confirmation means which creates said individual data, and wherein said individual data creation and confirmation means inputs healthy subject data for each diagnosis by a fetch-in function, maps cognitive data, creates a radar chart of data, compares data to data of a healthy subject, and applies discriminants to discriminate between organic brain damage, schizophrenia and depressive tendency.

7. A psychotic manifestation and mental state evaluation apparatus according to claim 6, wherein said individual data includes emotion item specified for specific stimulating image and reaction data and reaction-time data on stimulating image for each emotion item.

8. A psychotic manifestation and mental state evaluation apparatus according to claim 6, wherein said database stores three or more predetermined combinations, and individual data is provided for each of the three or more specific symptoms.

9. A psychotic manifestation and mental state evaluation apparatus according to claim 6, wherein when a specific symptom is discriminated, the evaluation is confirmed by using a discriminant that has been created in advance by reflecting plus value of attention data.

10. A psychotic manifestation and mental state evaluation apparatus according to claim 6, further comprising:

a display image creation means which displays a profile of said statistical data on stimulating image specified for said each specific emotion item and also displays a profile of healthy subjects for comparison.

11. A psychotic manifestation and mental state evaluation method comprising the steps of:
   storing, in a database, data of stimulating Noh mask images that express various kinds of human emotions according to changes of the angles at which the mask are photographed from the tilting up to tilting down;
   displaying the stimulating images;
   displaying questions, namely emotion items, about the feeling elicited by the stimulating images that have been one by one shown on an image display apparatus as well as displaying a response from a subject being evaluated to each question based on response data which includes affirmative response data, reaction data and a reaction-time value;
   gathering statistical data of the response to each emotion item with respect to the emotion elicited by each stimulating image; and
   evaluating, by processing means, psychotic manifestation and mental state based on the gathered statistical data including the number of affirmative responses, a number of expression evaluation variations, a balance coefficient of expression and a deviation score from healthy subjects' reference data that have been obtained by recalculating affirmative responses from each emotion item,
   wherein said database stores predetermined combinations of stimulating images photographed at different angles that have been selected from said stimulating images and plural emotion items that have been selected from said emotion items with respect to more than one psychotic manifestation and mental state,
   wherein said processing means collects a reaction value and a reaction-time value from the response data of the response to each emotion item that corresponds to each stimulating image, collects reaction data by comparing the reaction and reaction-time values with reference values, and collects attention data based on the reaction data with respect to each stimulating image, and evaluating psychotic manifestation and mental state based on the collected data, thereby creating attention data in regard to a specific emotion item with respect to a specific stimulating image,
   wherein the attention data, when used, permits said psychotic manifestation to be easily discriminated, said psychotic manifestation being one of organic brain damage, schizophrenia and depressive tendency,
   wherein said attention data with respect to specified stimulating image and specified emotion item has a three-dimensional structure in which plus values and minus values coexist and is displayed on said image display apparatus to permit a visual understanding of the condition of the subject,
   wherein after the collection, said processing means identifies a specific symptom that corresponds to said psychotic manifestation based on the attention data and a result of comparing the selected stimulating images and the emotion items to the stimulating image and emotion item stored in the database, and
   wherein individual data is created for each specific symptom by including a result of comparing the reaction data to the reaction data of healthy subjects for a specific emotion item with respect to a specific symptom.

12. A psychotic manifestation and mental state evaluation method according to claim 11, wherein said individual data includes emotion item specified for specific stimulating image and reaction data on stimulating image for each emotion item.

13. A psychotic manifestation and mental state evaluation method according to claim 11, wherein said database stores three or more predetermined combinations, and individual data is provided for each of the three or more specific symptoms.

14. A psychotic manifestation and mental state evaluation method according to claim 13, wherein when a specific symptom is discriminated, the evaluation is confirmed by using a discriminant that has been created in advance by reflecting plus value of attentive data.

15. A psychotic manifestation and mental state evaluation method according to claim 11, further comprising the steps of:
   displaying a profile of said statistical data on stimulating image specified for each specific emotion item; and
   displaying a profile of healthy subjects for comparison.

16. A psychotic manifestation and mental state evaluation method comprising the steps of:
   storing, in a database, data of stimulating Noh mask images that express various kinds of human emotions according to changes of the angles at which the masks are photographed from the tilting up to tilting down;
   displaying, on an image display apparatus, the stimulating images;
   displaying questions, namely emotion items, about the feeling elicited by the stimulating images that have been one by one shown on the image display apparatus as well as displaying a response, from a subject being evaluated, to each question based on response data which includes affirmative response data, reaction data and a reaction-time value;
   gathering statistical data of the response to each emotion item with respect to the emotion elicited by each stimulating image; and
   evaluating, by processing means, psychotic manifestation and mental state based on the gathered statistical data including the number of affirmative responses, a number of expression evaluation variations, a balance coefficient of expression and a deviation score from healthy subjects' reference data that have been obtained by recalculating affirmative responses from each emotion item,
   wherein said database stores predetermined combinations of stimulating images photographed at different angles that have been selected from said stimulating images and plural emotion items that have been selected from said emotion items with respect to more than one psychotic manifestation and mental state,
   wherein said processing means collects a reaction value and a reaction-time value from the response data of the response to each emotion item that corresponds to each stimulating image, collects reaction data and reaction-time data by comparing the reaction and reaction-time values with reference values, and collects attention data based on the reaction data with respect to each stimulating image, and evaluating psychotic manifestation and mental state based on the collected data, thereby creating attention data in regard to a specific emotion item with respect to a specific stimulating image
   wherein the attention data, when used, permits said psychotic manifestation to be easily discriminated, said psychotic manifestation being one of organic brain damage, schizophrenia and depressive tendency,
   wherein said attention data with respect to specified stimulating image and specified emotion item has a three-dimensional structure in which plus values and minus values coexist and is displayed on said image display apparatus to permit a visual understanding of the condition of the subject, wherein after the collection, said processing means identifies a specific symptom that corresponds to said psychotic manifestation based on the attention data and a result of comparing the selected stimulating images and the emotion items to the stimulating image and emotion item stored in the database, wherein individual data is created for each specific symptom by including a result of comparing the reaction data to the reaction data of healthy subjects for a specific emotion item with respect to a specific symptom, wherein said processing means includes individual data creation and confirmation means which creates said individual data, and wherein said individual data creation and confirmation means inputs healthy subject data for each diagnosis by a fetch-in function, maps cognitive data, creates a radar chart of data, compares data to data of a healthy subject, and applies discriminants to discriminate between organic brain damage, schizophrenia and depressive tendency.

17. A psychotic manifestation and mental state evaluation method according to claim 16, wherein said individual data includes emotion item specified for specific stimulating image and reaction data and reaction-time data on stimulating image for each emotion item.

18. A psychotic manifestation and mental state evaluation method according to claim 16, wherein said database stores three or more predetermined combinations, and individual data is provided for each of the three or more specific symptoms.

19. A psychotic manifestation and mental state evaluation method according to claim 16, wherein when a specific symptom is identified, the evaluation is confirmed by using an identity determining factor that has been created in advance by reflecting plus value of attention data.

20. A psychotic manifestation and mental state evaluation method according to claim 16, further comprising the steps of:
displaying a profile of said statistical data on stimulating image specified for each specific emotion item; and
displaying a profile of healthy subjects for comparison.

21. A computer program, stored on a storage medium, for evaluating a psychotic manifestation and mental state, wherein said computer program when executed causes a computer to perform the steps of:
storing, in a database, data of stimulating Noh mask images that express various kinds of human emotions according changes of the angles at which the masks are photographed from the tilting up to tilting down;
displaying the stimulating images;
displaying questions, namely emotion items, about the feeling elicited by the stimulating images that have been one shown on an image display apparatus as well as displaying a response, form a subject being evaluated, to each question based on response data which includes affirmative response data, reaction data and a reaction-time value;
gathering statistical data of the response to each emotion item with respect to the emotion elicited by each stimulating image; and
evaluating, by processing means, psychotic manifestation and mental state based on the gathered statistical data including the number of affirmative responses, a number of expression evaluation variations, a balance coefficient of expression and a deviation score from healthy subjects' reference data that have been obtained by recalculating affirmative responses from each emotion item, wherein said database stores predetermined combinations of stimulating images photographed at different angles that have been selected from said stimulating images and plural emotion items that have been selected from said emotion items with respect to more than one psychotic manifestation and mental state, wherein said processing means collects a reaction value and a reaction-time value from the response data of the response to each emotion item that corresponds to each stimulating image, collects reaction data by comparing the reaction and reaction-time values with reference values, and collects attention data based on the reaction data with respect to each stimulating image, and evaluating psychotic manifestation and mental state based on the collected data, thereby creating attention data in regard to a specific emotion item with respect to a specific stimulating image wherein the attention data, when used, permits said psychotic manifestation to be easily discriminated, said psychotic manifestation being one of organic brain damage, schizophrenia and depressive tendency, wherein said attention data with respect to specified stimulating image and specified emotion item has a three-dimensional structure in which plus values and minus values coexist and is displayed to permit a visual understanding of the condition of the subject, wherein after the collection, said processing means identifies a specific symptom that corresponds to said psychotic manifestation based on the attention data and a result of comparing the selected stimulating images and the emotion items to the stimulating image and emotion item stored in the database, and wherein individual data is created for each specific symptom by including a result of comparing the reaction data to the reaction data of healthy subjects for a specific emotion item with respect to a specific symptom.

22. A computer program, stored on a storage medium, for evaluating a psychotic manifestation and mental state, wherein said computer program when executed causes a computer to perform the steps of:
storing, in a database, data of stimulating Noh mask images that express various kinds of human emotions according to changes of the angles at which the masks are photographed from the tilting up to tilting down;
displaying, on an image display apparatus, the stimulating images;
displaying questions, namely emotion items, about the feeling elicited by the stimulating images that have been one by one shown on the image display apparatus as well as displaying a response, from a subject being evaluated, to each question based on response data which includes affirmative response data, reaction data and a reaction-time value;
gathering statistical data of the response to each emotion item with respect to the emotion elicited by each stimulating image; and
evaluating, by processing means, psychotic manifestation and mental state based on the gathered statistical data including the number of affirmative responses, a number of expression evaluation variations, a balance coefficient of expression and a deviation score from healthy subjects' reference data that have been obtained by recalculating affirmative responses from each emotion item, wherein said database stores predetermined combinations of stimulating images photographed at different angles that have been selected from said stimulating images and plural emotion items that have been selected from said emotion items with respect to more than one psychotic manifestation and mental state, wherein said processing means collects a reaction value and a reaction-time value from the response data of the response to each emotion item that corresponds to each stimulating image, collects reaction data by comparing the reaction and reaction-time values with reference values, and collects attention data based on the reaction data with respect to each stimulating image, and evaluating psychotic manifestation and mental state based on the collected data, thereby creating attention data in regard to a specific emotion item with respect to a specific stimulating image, wherein the attention data, when used, permits said psychotic manifestation to be easily discriminated, said psychotic manifestation being one of organic brain damage, schizophrenia and depressive tendency, wherein said attention data with respect to specified stimulating image and specified emotion item has a three-dimensional structure in which plus values and minus values coexist and is displayed to permit a visual understanding of the condition of the subject, wherein after the collection, said processing means identifies a specific symptom that corresponds to said psychotic manifestation based on the attention data and a result of comparing the selected stimulating images and the emotion items to the stimulating image and emotion item stored in the database, wherein individual data is created for each specific symptom by including a result of comparing the reaction data to the reaction data of healthy subjects for a specific emotion item with respect to a specific symptom, wherein said processing means includes individual data creation and confirmation means which creates said individual data, and wherein said individual data creation and confirmation means inputs healthy subject data for each diagnosis by a fetch-in function, maps cognitive data, creates a radar chart of data, compares data to data of a healthy subject, and applies discriminants to discriminate between organic brain damage, schizophrenia and depressive tendency.

23. A psychotic manifestation and mental state evaluation apparatus comprising:

a database which stores data of stimulating Noh mask images that express various kinds of human emotions according to changes of the angles at which the masks are photographed from tilting up to tilting down;

an image display apparatus for displaying the stimulating images;

means for displaying questions, referred to as emotion items, about the feeling elicited by the stimulating images that have been one by one shown on the image display apparatus as well as displaying a response from a subject being evaluated to each question;

means for gathering statistical data of the response to each emotion item with respect to the emotion elicited by each stimulating image; and processing means for evaluating psychotic manifestation and mental state based on the gathered statistical data, wherein said database stores predetermined combinations of stimulating images photographed at different angles that have been selected from said stimulating images and plural emotion items that have been selected from said emotion items with respect to more than one psychotic manifestation and mental state, wherein said processing means collects a reaction value and a reaction-time value from the response to each emotion item that corresponds to each stimulating image, collects reaction data by comparing the reaction and reaction-time values with reference values, and collects attention data based on the reaction data with respect to each stimulating image, thereby creating attention data in regard to a specific emotion item with respect to a specific stimulating image, wherein the attention data, when used, permits said psychotic manifestation to be easily discriminated, said psychotic manifestation being one of organic brain damage, schizophrenia and depressive tendency, wherein said attention data with respect to specified stimulating image and specified emotion item has a three-dimensional structure in which plus values and minus values coexist and is displayed on said image display apparatus to permit a visual understanding of the condition of the subject, wherein after the collection, said processing means identifies a specific symptom that corresponds to said psychotic manifestation based on the attention data and a result of comparing of the selected stimulating images and the emotion items to the stimulating image and emotion item stored in the database, wherein individual data is created for each specific symptom by including a result of comparing the reaction data to the reaction data of healthy subjects for a specific emotion item with respect to a specific symptom, wherein said processing means performs processing to filter people with depressive tendencies, wherein said processing to filter people with depressive tendencies includes:

a first step of comparing an average reaction time for all of the emotion items for each of the subjects being evaluated to a threshold of 2,800 ms to identify subjects whose average reaction time for all of the emotion items exceeds 2,800 ms, a second step of identifying subjects having depressive tendencies that require outpatient medication treatment among the subjects identified by said first step by determining for each subject whether a difference between the reaction time for negative emotion items including sadness, anger, hatred, weirdness, and fear and the reaction time for positive emotion items including happiness, shyness, and calmness for said subject exceeds 1,000 ms, and a third step of identifying subjects having depressive tendencies that can function in a school or work environment with counseling among the subjects identified by said first step by determining for each subject whether a difference between the reaction time for negative emotion items including sadness, anger, hatred, weirdness, and fear and the reaction time for positive emotion items including happiness, shyness, and calmness for said subject exceeds 500 ms but is less than 1,000 ms.

* * * * *